(12) United States Patent
Wu et al.

(10) Patent No.: US 10,774,359 B2
(45) Date of Patent: *Sep. 15, 2020

(54) CELLULAR ANALYSIS OF BODY FLUIDS

(71) Applicant: Abbott Laboratories, Abbott Park, IL (US)

(72) Inventors: Jiong Wu, Los Gatos, CA (US); Emily H. Lin, Cupertino, CA (US); Jihping Yang, Palo Alto, CA (US)

(73) Assignee: Abbott Laboratories, Abbott park, IL (US)

( * ) Notice: Subject to any disclaimer, the term of this patent is extended or adjusted under 35 U.S.C. 154(b) by 9 days.

This patent is subject to a terminal disclaimer.

(21) Appl. No.: 15/979,230

(22) Filed: May 14, 2018

(65) Prior Publication Data

US 2018/0334699 A1 Nov. 22, 2018

Related U.S. Application Data

(63) Continuation of application No. 13/720,615, filed on Dec. 19, 2012, now Pat. No. 9,970,045.
(Continued)

(51) Int. Cl.
*C12Q 1/04* (2006.01)
*G01N 33/50* (2006.01)

(52) U.S. Cl.
CPC ........... *C12Q 1/04* (2013.01); *G01N 33/5094* (2013.01)

(58) Field of Classification Search
CPC .............................. C12Q 1/04; G01N 33/5094
See application file for complete search history.

(56) References Cited

U.S. PATENT DOCUMENTS 4,325,706 A * 4/1982 Gershman .......... G01N 15/1459
356/39
4,485,175 A * 11/1984 Ledis ................. G01N 15/1209
436/10
(Continued)

FOREIGN PATENT DOCUMENTS

| EP | 1376135 | 5/2004 |
| EP | 1953526 | 8/2008 |
| WO | 01/36661 | 5/2001 |

OTHER PUBLICATIONS

Corberand (1996) "Reticulocyte analysis using flow cytometry" Hematol Cell Ther 38:487-494.
(Continued)

*Primary Examiner* — Joseph G. Dauner
(74) *Attorney, Agent, or Firm* — Edward J. Baba; Bozicevic Field & Francis LLP

(57) ABSTRACT

Herein is provided a simple, reliable and accurate method for cellular analysis on hematology analyzers. In various aspects, the methods provide separation and/or differentiation between red blood cells (RBCs) and white blood cells (WBCs) by utilizing a fluorescent dye to selectively stain WBCs such that they emit stronger fluorescence signals. The method provides optimal detection limits on WBCs and RBCs, thereby allowing analysis of samples with sparse cellular concentrations. As few as one reagent may be used to prepare a single dilution for body fluid analysis, in order to simplify the body fluid analysis. Minimal damage to WBCs is attained using the lysis-free approach described in aspects of the disclosure.

16 Claims, 17 Drawing Sheets

Related U.S. Application Data

(60) Provisional application No. 61/580,623, filed on Dec. 27, 2011.

(56) References Cited

U.S. PATENT DOCUMENTS

| | | | |
|---|---|---|---|
| 4,981,803 A | 1/1991 | Kuroda | |
| 5,436,134 A | 7/1995 | Haugland et al. | |
| 5,686,308 A * | 11/1997 | Li | G01N 33/5094 436/10 |
| 5,691,204 A | 11/1997 | Kim et al. | |
| 5,693,484 A | 12/1997 | Nakamoto et al. | |
| 5,812,419 A | 9/1998 | Chupp et al. | |
| 6,008,052 A | 12/1999 | Davis et al. | |
| 6,911,313 B2 | 6/2005 | Houwen et al. | |
| 9,091,624 B2 * | 7/2015 | Wu | G01N 15/1459 |
| 9,103,759 B2 * | 8/2015 | Wu | G01N 15/1434 |
| 9,970,045 B2 * | 5/2018 | Wu | G01N 33/5094 |
| 2004/0241770 A1 | 12/2004 | Houwen et al. | |
| 2007/0231913 A1 | 10/2007 | Tsuji et al. | |
| 2010/0248247 A1 | 9/2010 | Kataoka et al. | |
| 2011/0070606 A1 | 3/2011 | Winkelman et al. | |
| 2011/0275064 A1 | 11/2011 | Wu et al. | |
| 2012/0282598 A1 * | 11/2012 | Wu | G01N 15/1459 435/6.1 |
| 2012/0282599 A1 * | 11/2012 | Wu | G01N 15/1434 435/6.1 |

OTHER PUBLICATIONS

Graham and Galloway (2001) "The laboratory diagnosis of urinary tract infection" J Clin Pathol 54:911-919.

Marra et al. (2004) "Cerebrospinal Fluid Abnormalities in Patients with Syphilis: Association with Clinical and Laboratory Features" The Journal of Infectious Diseases 189:369-376.

Oster (1955) "Dye Binding to High Polymers" Journal of Polymer Science vol. XVI:235-244.

Van Acker et al. (2001) "Automated Flow Cytometric Analysis of Cerebrospinal Fluid" Clinical Chemistry 47(3):556-560.

* cited by examiner

CELLULAR ANALYSIS OF BODY FLUIDS

CROSS REFERENCE TO RELATED APPLICATIONS

This application is a continuation of U.S. patent application Ser. No. 13/720,615, filed on Dec. 19, 2012, issued as U.S. Pat. No. 9,970,045, which claims priority benefit to the filing date of U.S. Provisional Patent Application Ser. No. 61/580,623, filed on Dec. 27, 2011, the disclosures of which are herein incorporated by reference in their entirety.

BACKGROUND

A variety of methods are used for cellular analysis, including visual and/or automated inspection via light or fluorescent light microscopy. Cellular examinations and analyses of these types are commonly practiced in order to obtain information regarding cell lineage, maturational stage, and cell counts in a sample.

Flow cytometry is a method for identifying and distinguishing between different cell types in a non-homogeneous sample. In the flow cytometer, cells are passed one at a time or nearly one at a time through a sensing region where each cell is irradiated by an energy source. Typically, single wavelength light sources (e.g., lasers, etc.) are used as the energy source and one or more of a variety of sensors record data based on the interaction of the cells with the applied energy. Flow cytometry is commonly used in hematology and has been particularly successful in the diagnosis of blood cancers. In addition to flow cytometry, other analytical methods are used in hematology and in characterizing a population of cells.

Blood samples tend to have a high concentration of cells. Analysis of samples with significantly lower concentrations of cells, whether by flow cytometry or other techniques, is more difficult and therefore less common. In addition, traditional hematology analyzers, which are designed to measure whole blood samples, tend to have limited detection sensitivity for low-end cell concentrations. In some cases, manual examination of samples is the only available method for cellular analysis. Improved methods for analyzing samples with low cell counts are desirable in the fields of medicine, microbiology, and others.

SUMMARY

In one aspect, the disclosure provides a method for analyzing a body fluid containing cells, the method comprising: staining the body fluid with a fluorescent dye, wherein the fluorescent dye permeates a cell membrane and binds to a nucleic acid to form a dye complex within the cell; irradiating the stained body fluid with energy from an energy source; and measuring a fluorescence signal emitted by the dye complex in the stained body fluid.

In some such aspects, the body fluid comprises less than about 20 cells/µL.

In some such aspects, the body fluid comprises more than about 20 cells/µL.

In some such aspects, the nucleic acid is selected from a DNA and RNA.

In some such aspects, the energy source provides monochromatic light having a wavelength in the visible spectrum, and wherein the wavelength of the monochromatic light and the wavelength of the fluorescence signal are different.

In some such aspects, unbound fluorescent dye emits less fluorescent light when irradiated with energy from the energy source compared with the dye complex.

In some such aspects, unbound fluorescent dye does not fluoresce when irradiated with energy from the energy source while unbound to the nucleic acid, such that cells lacking the dye complex do not emit a fluorescence signal.

In some such aspects, the method comprises differentiating cells with nuclei from cells without nuclei based on the presence or absence of the fluorescent dye.

In some such aspects, the measuring involves enumerating and differentiating RBCs and WBCs.

In some such aspects, the method does not involve lysing RBCs prior to the measuring.

In some such aspects, the body fluid comprises intact WBCs and RBCs.

In some such aspects, the measuring is carried out using an automated hematology analyzer, flow cytometer, or other diagnostic analyzer for body fluid samples.

In some such aspects, the measuring comprises flowing the body fluid through a flow cell in a cytometer.

In some such aspects, the fluorescent dye is provided in a composition that further comprises water.

In another aspect, the disclosure provides a method for analyzing a fluid, wherein the fluid contains less than about 40 cells/µL, the method comprising: contacting the fluid with a fluorescent dye, wherein the fluorescent dye permeates a cell membrane and binds to a nucleic acid to form a dye complex within the cell; irradiating the fluid with energy from an energy source; and measuring a fluorescence signal emitted by the dye complex in the fluid.

In some such aspects, the fluid contains less than about 20 cells/µL.

In some such aspects, the fluid contains less than about 5 cells/µL.

In some such aspects, the fluid is a body fluid.

In some such aspects, the fluid is a biological fluid.

In another aspect, the disclosure provides a method for differentiating cells, the method comprising: contacting the cells with a solution comprising a fluorescent dye, wherein the fluorescent dye is water soluble, capable of permeating a cell membrane, and capable of binding to a nucleic acid; irradiating the cells with an excitation light from an excitation light source; and measuring light emissions from the cells and differentiating cells containing nucleic acids from cells lacking nucleic acids based on the measuring.

In another aspect, the disclosure provides a composition for analyzing a body fluid, the composition comprising water and a fluorescent dye, wherein the fluorescent dye is water soluble, capable of permeating a cell membrane, and capable of binding to a nucleic acid.

In another aspect, the disclosure provides a hematology system comprising: a sample holder for holding a sample to be analyzed; a mixing receptacle for mixing at least a portion of the sample to be analyzed with a staining composition; a storage receptacle for storing the staining composition, wherein the staining composition comprises a dye capable of permeating a cell membrane and binding to a nucleic acid, and wherein the dye is fluorescent when bound to a nucleic acid; a flow cell; at least one energy source for applying electromagnetic energy to the flow cell; one or more detectors for detecting fluorescence originating from within the flow cell; and one or more visible light detectors for detecting scattered visible light.

In some such aspects, the system comprises an aspirating mechanism for aspirating at least a portion of the sample to be analyzed from the sample holder to the mixing receptacle.

In some such aspects, the system comprises an aspirating mechanism for aspirating staining composition from the storage receptacle to the mixing receptacle.

In some such aspects, the at least one energy source provides monochromatic light at a wavelength λ1.

In some such aspects, the dye absorbs light at wavelength λ1 and emits light at wavelength λ2 when the dye is bound to a nucleic acid.

In some such aspects, the detector detects light at wavelength λ2.

In some such aspects, the system comprises at least one additional energy source for providing non-monochromatic visible light.

In some such aspects, the sample to be analyzed is a body fluid.

In another aspect, the disclosure provides a method for preparing a hematology system, the method comprising: providing a mixing receptacle for mixing at least a portion of a sample to be analyzed with a staining composition; providing a storage receptacle for storing the staining composition, wherein the staining composition comprises a dye capable of permeating a cell membrane and binding to a nucleic acid, and wherein the dye is fluorescent when bound to a nucleic acid; providing a flow cell; positioning an energy source for providing electromagnetic energy to the flow cell; positioning a detector for detecting fluorescence emitted from within the flow cell.

In another aspect, the disclosure provides a method for preparing a receptacle for use in analyzing a body fluid, the method comprising adding to the receptacle a composition comprising a dye capable of permeating a cell membrane and binding to a nucleic acid, wherein the dye is fluorescent when bound to a nucleic acid, and wherein the receptacle is an integrated or modular part of a hematology system.

DETAILED DISCLOSURE

Definitions

Figure 1:
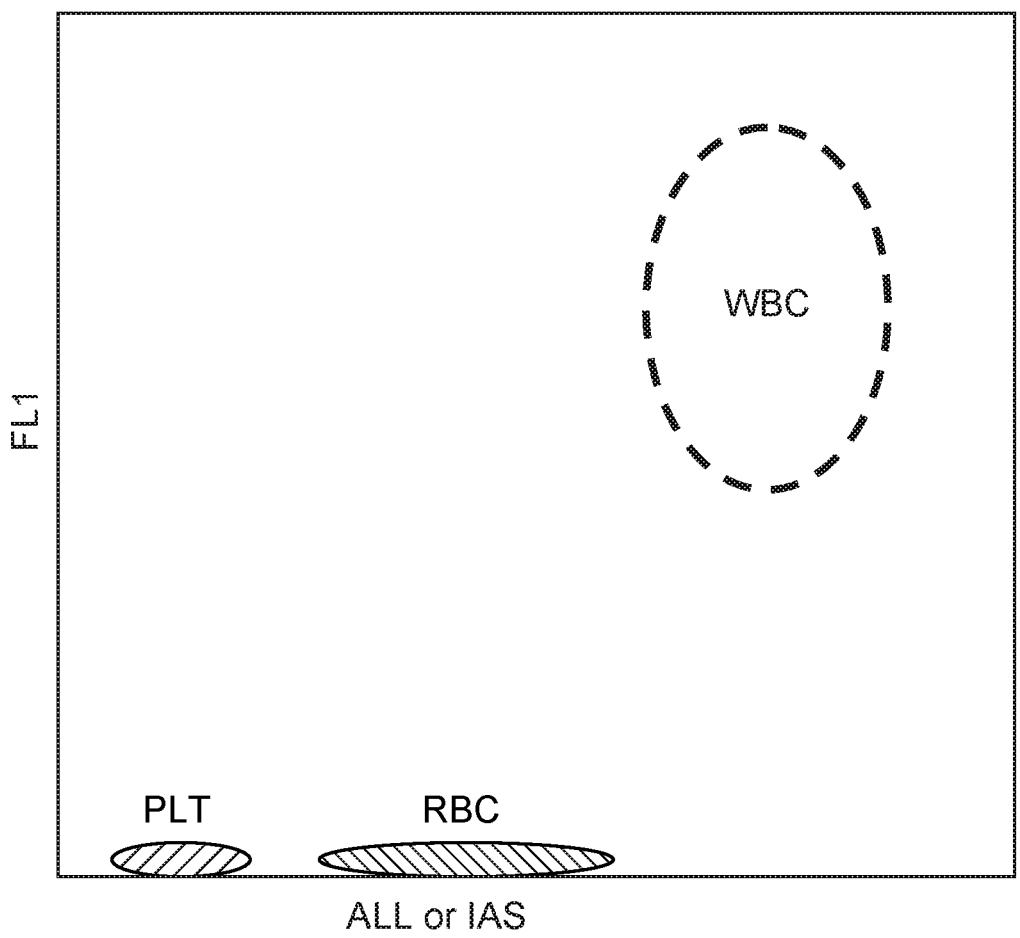
FIG. 1 provides a schematic image of an aspect of a body fluid analysis method described herein. WBCs are separated from RBCs upon DNA-dye interaction and subsequent emission of fluorescence. The fluorescence information, as well as other optical scattering signals, are used in cellular analysis of body fluid samples. FL1 indicates the fluorescence collected with a 530±20 nm band path filter. ALL and IAS are the light scattering signals collected at 0 to 1 degrees and 3 to 10 degrees, respectively.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein. It is understood that the present disclosure supersedes any disclosure of an incorporated publication to the extent there is a contradiction.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The term "typically" is used to indicate common practices of the invention. The term indicates that such disclosure is exemplary, although (unless otherwise indicated) not necessary, for the materials and methods of the invention. Thus, the term "typically" should be interpreted as "typically, although not necessarily." Similarly, the term "optionally," as in a material or component that is optionally present, indicates that the invention includes instances wherein the material or component is present, and also includes instances wherein the material or component is not present.

As used herein, the term "body fluid" refers to fluids present or obtained from an animal, including fluids such as cerebrospinal fluid, peritoneal fluid, pericardial fluid, pleural fluid, synovial fluid, urine, saliva, tears, semen, amniotic fluid, sputum, and the like, as well as fluids obtained from cysts, tumors, and the like. Unless otherwise specified, the term "body fluid" does not include whole blood, although a body fluid may contain red blood cells (RBCs) and/or white blood cells (WBCs).

In some aspects, the disclosure provides methods and materials for analyzing fluids with low cell count. By low cell count is meant fluids that have less than about 100 cells/µL, or less than about 80 cells/µL, or less than about 60 cells/µL, or less than about 40 cells/µL, or less than about 30 cells/µL, or less than about 20 cells/µL, or less than about 10 cells/µL, or less than about 5 cells/µL. In some embodiments, such low cell count is the result of dilution of a more concentrated original sample. In other embodiments, such low cell count is a natural characteristic of the fluid to be analyzed (i.e., no dilution is necessary to achieve the low cell count).

The fluids to be analyzed using the methods and materials described herein are, in some embodiments, selected from a body fluid. In other embodiments, the fluids to be analyzed are biological in nature but are not body fluids. In some embodiments, the fluid to be analyzed is "synthesized," meaning that a population of cells is added to a fluid, wherein the fluid is biologically compatible but is not the fluid in which the cells are normally found. Examples of such fluids include buffered aqueous solutions and the like.

Materials

In some embodiments, the methods of interest involve contacting a population of cells with a labeling composition suitable to aid in the desired characterization of the cells. In some embodiments the labeling composition comprises a fluorescent dye, and optionally further comprises additional components such as those described herein below. The components of the labeling composition and the relative concentration of such components may be varied according to the needs and requirements of the intended use. The labeling composition, with or without the dye present, may alternatively be referred to herein as "reagent."

The methods and materials of interest involve a fluorescent dye (also referred to herein as a "dye"). The fluorescent dye may be any suitable dye having the characteristics necessary or suitable to carry out the methods of interest. For example, in some embodiments, the dye is water soluble. For example, in some embodiments, the fluorescent dye has an aqueous solubility of at least 1 µg/L, or at least 5 µg/L, or at least 10 µg/L, or at least 20 µg/L, or at least 50 µg/L. In some embodiments, the dye is stable in aqueous solutions, meaning that the dye does not significantly degrade on the timescale suitable for the methods of analysis described herein. For example, the dye is stable in a buffered aqueous solution (e.g., cell reagent) at ambient temperatures (e.g., approximately 20-25° C.) for at least 30 min, or at least 1 hr or at least 6 hr, or at least 12 hr, or at least 24 hours, or at least 2 days, or at least 7 days, or at least 1 month. Also for example, the dye is stable in a buffered aqueous solution (e.g., cell reagent) under refrigeration (e.g., below approximately 10° C.) for at least 1 hr, or at least 12 hr, or at least 24 hours, or at least 2 days, or at least 7 days, or at least 1 month, or at least 6 months, or at least 12 months.

In some embodiments, the dye is able to penetrate a cell membrane, such as the walls of blood cells or the like. In some embodiments, the dye is further able to penetrate a cell nucleus once inside a cell.

In some embodiments, the dye binds to a nucleic acid. In some embodiments, the dye binds to DNA. In some embodiments, the dyes of interest bind to DNA but do not bind to RNA. In some embodiments, the dyes of interest bind preferentially to DNA over RNA. In some embodiments, binding of the dye to a DNA molecule involves hydrogen-bonding or another non-covalent interaction. In some embodiments, the dye binds to a single strand of DNA or a single strand of a double-stranded DNA complex. In some embodiments, the dye binds to both strands of a double-stranded DNA complex.

Throughout this specification, a dye bound to DNA is referred to as a dye complex. In some embodiments, the dye binds to DNA with a high affinity and a high binding constant. In some embodiments, and as mentioned herein, the affinity and concentration of the dye is great enough that the dye is sufficient to "stain" (post penetration and DNA-binding) at least 250,000 cells/µL.

In some embodiments, the dye is fluorescent. Thus, the dye absorbs incident light at one wavelength or one group of wavelengths around a peak absorption wavelength (also referred to as a peak excitation wavelength), and emits light at another wavelength or at a group of wavelengths around a peak emission wavelength. In some embodiments, the peak absorption wavelength is different from the peak emission wavelength. Furthermore, in some embodiments, the peak adsorption wavelength and/or the peak emission wavelength is/are dependent upon the environment of the dye. For example, in some embodiments, the peak absorption wavelength and/or peak emission wavelength for a dye bound to DNA (i.e., a dye complex) differs from the peak adsorption wavelength and/or peak emission wavelength for an unbound dye.

In some embodiments, the peak adsorption wavelength and the peak emission wavelength for a dye complex differ by at least 10 nm, or at least 15 nm, or at least 20 nm, or at least 25 nm, or at least 30 nm, or at least 35 nm, or at least 40 nm, or at least 45 nm, or at least 50 nm. In some embodiments, the peak absorption wavelength for a dye complex is in the range of 400-700 nm. For example, in some embodiments the peak absorption is in the range of 425-550 nm, or in the range of 450-525 nm, or in the range of 475-500 nm, or in the range of 480-495 nm, or in the range of 485-490 nm. Also for example, in some embodiments the peak absorption is in the range of 500-700 nm, or in the range of 550-675 nm, or in the range of 600-650 nm, or in the range of 620-640 nm.

In some embodiments, the peak emission wavelength for a dye complex is in the range of 425-800 nm, such as in the range of 425-700 nm. For example, in some embodiments, the peak emission is in the range of 450-650 nm, or in the range of 475-625 nm, or in the range of 500-550 nm, or in the range of 510-540 nm, or in the range of 520-530 nm.

For example, in some embodiments the fluorescent dye is selected from thiazole orange or 1-methyl-4-[(3-methyl-2-(3H)-benzothiazolylidene)methyl]quinolinium p-tosylate, thiazole blue, 4-[(3-methyl-2-(3H)-benzothiazolylidene)methyl]-1-[3-(trimethylammonium)propyl]quinolinium diiodide, 3,3'-dimethyloxacarbocyanine iodide or 3-methyl-2-[3(3-methyl-2(3H)-benzothiazolylidene-1-propenyl] benzoxazolium iodide, thioflavine T, the stains SYTO® and TOTO® (Life Technologies), ethidium bromide, propidium iodide, acridine orange, coriphosphine O, auramine O, the stains HOECHST 33258 (2'-(4-hydroxyphenyl)-5-(4 methyl-1-piperizinyl)-2,5'-bi-1H-benzimidazole trihydrochloride hydrate) and HOECHST 33342® (2'-(4-ethoxyphenyl)-5-(4-methyl-1-piperizinyl)-2,5'-bi-1H-benzimidazole trihydrochloride), 4' 6-diamino-2-phenylindole dihydrochloride (DAPI), 4',6-(diimidazolin-2-yl)-2-phenylindole dihydrochloride (DIPI), 7-aminoactinomycin D, actinomycin D, and LDS 751 (2-(4-(4-dimethylaminophenyl)-1,3-butadienyl)-3-ethylbenzoth iazolium perchiorate), or a dye sold under the tradename SYBR® (Life Technologies, e.g., SYBR Green, SYBR Gold, SYBR 11, etc.), or the like.

In some embodiments, in addition to a dye as described above, a labeling composition of interest further comprises one or more of the components identified in the following paragraphs. It will be appreciated that the lists below are representative only, and that substitutions may be made when desired using chemically and/or biologically equivalent materials.

In some embodiments, the labeling composition contains a surfactant or detergent. Ionic and neutral surfactants can be employed. For example, zwitterionic surfactants such as steroidal glucosides (e.g., Big CHAP, Big Doxy CHAP, etc.) and glucopyranosides, as well as other surfactants known in the art may be used. Surfactants can be present in the labeling composition in any suitable amount, such as 0.0001-0.1% (w/v).

In some embodiments, the labeling composition further contains a buffer or pH modifier. Examples of buffers or pH modifiers include, but are not limited to, PBS, MOPS, and HEPES. Additional examples of buffers or pH modifiers include: acids such as hydrochloric acid, hydrobromic acid, acetic acid, phosphoric acid, and the like; bases such as sodium hydroxide, sodium carbonate, sodium bicarbonate, organic amines (e.g., imidazole, triethylamine, etc.), and the like; and salts such as sodium chloride, calcium chloride, and the like. For example, an organic buffer material such as imidazole may be present in the labeling composition at a concentration in the range of about 0.001-3% (w/v). Also for example, an inorganic material such as HCl may be present in a concentration in the range of about 0.001-5% (w/v). Similarly, a salt such as NaCl may be present at a concentration in the range of about 0.001-3% (w/v). As mentioned previously, equivalents of such materials are known and may be substituted where appropriate.

In some embodiments, the methods and materials of interest further involve additional components as necessary or desired. Examples of such additional components include colorants, preservatives, anti-microbial agents, osmolality adjustors, and co-solvents.

For example, an anti-microbial agent such as Proclin (e.g., Proclin 150, 200, 300, etc.), vancomycin, penicillin, and the like may be present. The anti-microbial agent may be present at a concentration in the range of about 0.001-0.5% (w/v).

In some embodiments, stock solutions of various components may be made during preparation of the labeling compositions of interest. For example, stock solutions of the any component (e.g., dye compound, etc.) can be made, such as to aid in solubilizing the components or to accurately measure the component volumes. Stock solutions can be made using water as solvent, or using an organic solvent such as dimethyl sulfoxide, isopropanol, ethanol, or methanol, or using a combination thereof.

In some embodiments, the methods and materials of interest involve an aqueous solution of the above-identified components. It will be appreciated that the concentration of the various components present in the labeling composition can vary according to the intended use. The paragraphs above and below provide some guidelines for concentrations of materials present in the labeling composition. As indicated herein, in some embodiments the labeling composition is combined with a fluid to be analyzed (e.g., a body fluid). Accordingly, although the guidelines provided herein refer to amounts of various components as present in the labeling composition, it will be appreciated that such guidelines are also applicable to the combination of the labeling composition and the fluid to be analyzed (i.e., in some embodiments, the material that is actually analyzed in a hematology analyzer as described herein will contain similar percentages and relative amounts of the various components).

In some embodiments, the dye is present in the labeling composition in a predetermined concentration. It will be appreciated that the predetermined concentration may vary depending on the identity of the dye (i.e., the chemical structure, binding affinity for the nucleic acid target, etc.) as well as the operating parameters of the analyzer to be used. In some embodiments, the dye component is present in an amount necessary to stain at least the number of cells present in the body fluid, such as 10 cells/µL or greater, or 50 cells/µL or greater. For example, the dye is present in an amount necessary to stain 100,000 cells/µL or greater, or 200,000 cells/µL or greater, or 250,000 cells/µL or greater. In some embodiments, the amount of dye compound present is in the range of 0.000001-0.5%, or 0.00001-0.5%, or 0.0001-0.5%, or 0.001-0.1% (w/v).

In some embodiments, an organic buffering agent is present in the labeling composition. Examples of such a material include organic amines, such as triethylamine, trimethylamine, and cyclic amines such as imidazole, and the like. The organic buffering agent (along with any other buffers) may be present in an amount necessary to create and maintain a desired pH in the analyte composition.

In some embodiments, the labeling composition containing a dye of interest is isotonic or substantially isotonic (i.e., within about 20% of isotonic, or within about 10% of isotonic, or within about 5% of isotonic). In some embodiments, the labeling composition containing a dye of interest has neutral pH or substantially neutral pH (i.e., within a pH range of about 6-8, or about 6.5-7.5). These characteristics of the labeling composition aid in reducing damage to cells of any type during sample preparation and analysis, and therefore result in more accurate cellular analysis of body fluid samples.

Methods

In some embodiments, the methods of interest involve contacting the population of cells with the labeling composition. In some such embodiments, the contacting involves mixing the labeling composition with a fluid (e.g., a body fluid) containing the cells to be analyzed. Thus, in some embodiments the methods of interest involve diluting a fluid sample containing cells with a labeling composition, wherein the labeling composition comprises water and a dye, and optionally comprises other components such as those provided herein. In some such embodiments, the methods involve a single dilution step (i.e. adding the labeling composition to the fluid sample only once) at a predetermined dilution ratio that provides an optimal concentration of analyte for fluorescence detection and measurement.

In some embodiments, because the dyes of interest bind to DNA, cells that lack DNA are not able to form a dye complex when exposed to the dye. Cells lacking DNA that have been exposed to the dye therefore do not exhibit the emission characteristics of the dye complex when analyzed using the methods described herein (e.g., when exposed to a fluorescence excitation energy source) or only emit minimal or weak fluorescence due to autofluorescence. In contrast, cells that contain DNA are able to form a dye complex. Such cells, when stained with a dye of interest, exhibit the emission characteristics of the dye complex when analyzed using the methods described herein. In view of this distinction, in some embodiments the methods of interest provide a means for differentiating cells containing DNA from cells that lack DNA. In some embodiments, the methods of interest also provide a means for differentiating cells containing a nucleus from cells lacking a nucleus, particularly when the nucleus contains DNA. In some embodiments, the differentiation is provided based on fluorescence measurements that either observe fluorescence from a cell (indicating the presence of DNA and possibly indicating the presence of a nucleus) or do not observe fluorescence from a cell (indicating the lack of DNA and possibly indicating the lack of a nucleus in the cell). Also, non-cellular events (e.g., non-cellular objects that lack DNA) present in the fluid being analyzed are differentiated by the lack of characteristic fluorescence emission.

For example, when RBCs are exposed to the dye, mature RBCs (which lack a nucleus and lack DNA) do not form the dye complex. Therefore, RBCs exposed to the dye do not exhibit the emission characteristics of the dye complex when analyzed using the methods described herein. In contrast, WBCs contain a nucleus and DNA, and therefore form the dye complex when exposed to the dye. In some embodiments, therefore, the methods of interest allow differentiation of WBCs from RBCs in a sample containing such cells. The differentiation is based on the presence or absence of a fluorescent signal indicative of the formation of the dye complex.

In addition to differentiation as described above, the formation of the dye complex between a dye of interest and DNA also allows for enumeration of cells containing DNA in a fluid sample containing cells. For example, the methods of interest include enumerating WBCs in a fluid sample containing such cells. Enumeration is based on observation of fluorescence indicative of the formation of the dye complex in a method suitable for counting cells. Suitable methods include automated hematology analyzers such as flow cytometers and other fluorescence-based cell counting methods.

As mentioned herein, the methods of interest allow for enumeration and differentiation of WBCs in a sample containing WBCs and other objects (e.g., RBCs and non-cellular events). In some embodiments, the sample is a fluid such as a body fluid, and contains a very low concentration of cells as described in more detail herein. In some embodiments, the methods of the present disclosure further allow for classification of WBCs into 2-part, 3-part or 5-part differentials using multi-angle scattering technologies. In certain embodiments, RBCs can be further separated from other non-RBC particles using multi-angle scattering technologies.

In some embodiments, the methods of interest do not involve a lysing agent and do not involve lysing cells prior to recording data. For example, the methods of interest do not involve adding a lysing agent to the fluid sample containing cells prior to analysis of the fluid sample. Thus, in some embodiments, the labeling composition does not contain a lysing agent. The fluid samples that are analyzed are not lysates and do not contain cellular contents that have been released from a cell via lysis. In some embodiments, the fluid samples to be analyzed contain intact RBCs and such RBCs are not lysed prior to fluorescence measurements. By "lysing agent" is meant to include any materials that cause significant cell lysis, particularly (but not limited to) RBC lysis. Lysing agents include, but are not limited to, various types of surfactants, enzymes, antibodies, pH adjusting agents, osmolytes (osmolality adjusting agents), and the like that are known in the art or later discovered.

Because lysing agents are not involved in the preparation of fluid samples to be analyzed, WBCs present in the fluid are not damaged as they would or might be were lysing agents employed. This is particularly advantageous in body fluids containing WBCs, because the WBCs contained therein are typically more fragile than WBCs in whole blood.

As mentioned above, in some embodiments the methods of interest involve dilution with a predetermined amount of labeling composition to provide a desired dilution ratio and a desired analyte concentration. The predetermined amount may be determined based on detection limits in the apparatus used for analysis of the fluid sample. In some embodiments, the detection limit is optimized by adjustments to the sample injection rate (relative to the flow cell rate), measurement duration, and the like. For example, a prototype analyzer with 1:10 (blood:reagent) dilution ratio, 4.0 µL per second injection rate, and 60 seconds sample measurement (data collection), would result in a collection of approximately 240 events for a sample at 10 cells per µL, sufficient for supporting precise cellular analysis.

In some embodiments, the methods of interest are suitable for analyzing any fluid sample with WBCs. As mentioned previously, such fluid samples include body fluids, and also include other fluid samples such as prepared aqueous solutions of cells, plant-based and plant-derived solutions, and like, particularly where such sample fluids contain low cell counts (e.g., less than 40 cells/µL, or less than 30 cells/µL, etc.).

In some embodiments, the methods of interest provide a simple, reliable, and accurate means for enumerating and differentiating WBCs in a sample fluid containing WBCs and optionally containing RBCs. Fluorescence detection using automated hematology analyzers ensures accuracy and reliability, and the use of single-step dilution provides simplicity in sample preparation. The sample fluid containing cells is stained with a fluorescent label contained in a labeling composition, wherein the fluorescent label permeates cell walls and binds to DNA to create a dye complex. Stained WBCs emit fluorescent emission signals indicative of the dye complex, whereas RBCs do not emit such signals or emit such signals at a significantly lower intensity. The labeling composition is free of lysing agents and no lysing agents are added to the sample fluid, thereby protecting the WBCs present. Optimal detecting limits are determined by adjustment of variables including sample flow rate, detection frequency, and the like.

Additional aspects of methods for analyzing WBCs and systems for performing such methods can be found in U.S. Provisional Patent Application Ser. No. 61/482,541, filed May 4, 2011, as well as U.S. Provisional Patent Application Ser. No. 61/482,549, filed May 4, 2011, the disclosures of which are incorporated by reference herein in their entireties.

Output and Advantages

In some embodiments, analysis of the dyed fluids results in a variety of information suitable for multi-dimensional data analysis, graphs, and the like. For example, in some embodiments, the methods described herein provide an accurate total WBC count. In some embodiments, the methods provide data as to the relative proportions of different types of WBCs in a sample (e.g., cell counts of neutrophils, eosinophils, basophils, lymphocytes, and/or monocytes, or various combinations thereof). Such data may be used, for example, as diagnostic information in treating patients.

As mentioned herein, in some embodiments the methods of interest involve selectively staining WBCs in a fluid sample by introducing a dye that selectively binds to DNA and fluoresces when so bound. Accordingly, analysis of a stained sample fluid includes recording the stronger fluorescence emissions that originate from cells containing a dye complex (e.g., WBCs) compared with the weak or non-existent fluorescence emissions that originate from cells lacking the dye complex (e.g., RBCs). The fluorescence measurements can be obtained using, for example, multi-channel optical scattering analyzers.

In some embodiments, the materials and methods of interest allow for cellular analysis of body fluids and other fluids useful, for example, in medical diagnostics. Cellular analysis of fluid samples with very low cell counts (e.g., less than 40 per µL, or less than 10 per µL, etc.) is enabled by the methods herein, including body fluids having particularly fragile cells. The simplicity of the methods allows such samples to be analyzed within 1-2 hours after sample draw from a patient, which also aids in analysis of fragile cells. The lack of cell lysing agents in the compositions and methods described herein further adds to the ability to analyze samples containing fragile cells. Damage to fragile cells in the fluids of interest potentially results in inaccurate analysis such as inaccurate cell counts and cellular differentiation.

The optimal dilution ratios offered by the methods described herein are a further improvement over traditional hematological analysis. For example, the dilution ratios (i.e. blood:diluent=1:300 for RBC dilution) used by traditional hematology analyzers are not sensitive enough to support measuring samples with very low cellular concentrations. In contrast, in some embodiments, the methods herein allow a single dilution to provide an optimal dilution ratio for optimal fluorescence detection.

The methods of the present disclosure are simple, e.g., in some embodiments, only a single reagent and a single dilution are required. In some embodiments, the dilution ratios can be easily adjusted and/or optimized. Furthermore, the methods of the present disclosure are simple to implement, and can be performed, e.g., on a traditional hematology analyzer, without the need for extensive adjustments and/or modifications.

These and other advantages will be apparent to one of skill in the art based on the disclosure provided herein, including the examples below.

EXAMPLES

General Testing Procedure: (A) Modify flow script and algorithm of a CELL-DYN Sapphire hematology analyzer to allow it to be used for a body fluid assay. (B) All body fluid (BF) assays are conducted using (slightly modified) WBC extended counting mode: BF sample aspiration (~120 µL), followed by sample (BF) to reagent (Sapphire reticulocyte reagent) mixing, ratio at 1 to 35, followed by mixed sample incubation (40° C.×25 sec), followed by incubated sample delivered to flow cell for measurement (32 sec measurement), followed by data collection, raw data recorded as .fcs files, followed by use of software such as FCS Express to analyze the raw data.

All reference results were measured using standard manual chamber counting procedures.

Reagent was formulated using the following components and concentrations:

| Component | Concentration[1] |
| --- | --- |
| Imidazole | 0.3400% |
| 1N HCl | 2.5325% |
| NaCl | 0.6800% |
| Proclin 300 | 0.0315% |
| BIGCHAP | 0.0050% |
| SYBR 11 | 0.0002% |
| DMSO[2] | 0.0220% |
| Water | To 100% |

[1]1% = 1 g/100 mL
[2]DMSO (dimethyl sulfoxide) was used to make a stock solution of the dye component.

Example 1

Analysis of Low Cell Count Samples

A prototype analyzer with 1:35 (blood:reagent) dilution ratio, 2.3 µL per second injection rate, and 32 seconds sample measurement (data collection), results in a collection of more than 20 events for a sample at 10 cells per µL.

Figure 2A:
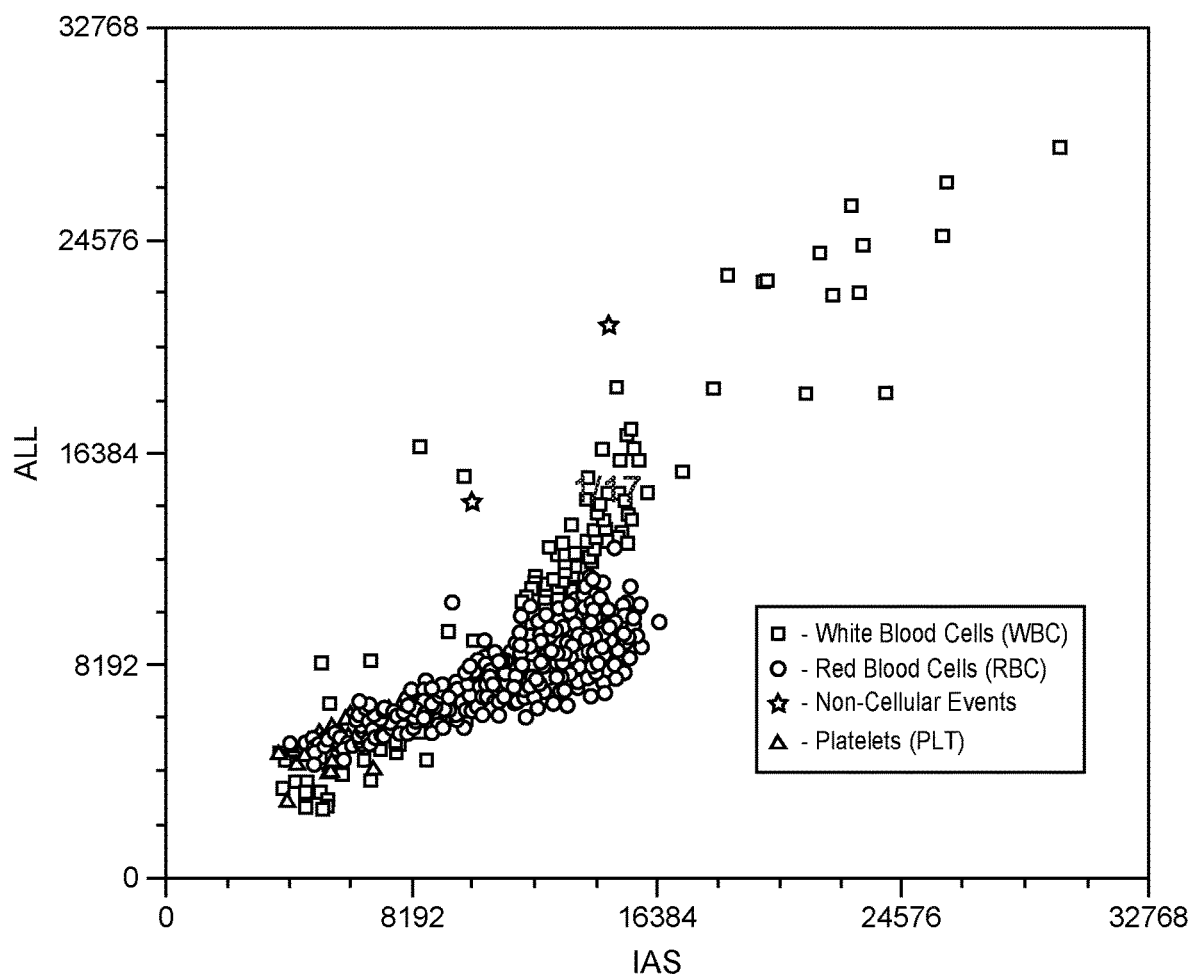
FIG. 2A is a scattergram (ALL v. IAS) of cellular analysis for a body fluid sample. WBC=89/µL (reference=81/µL); RBCs=2012/µL (reference=1733/µL).
Figure 2B:
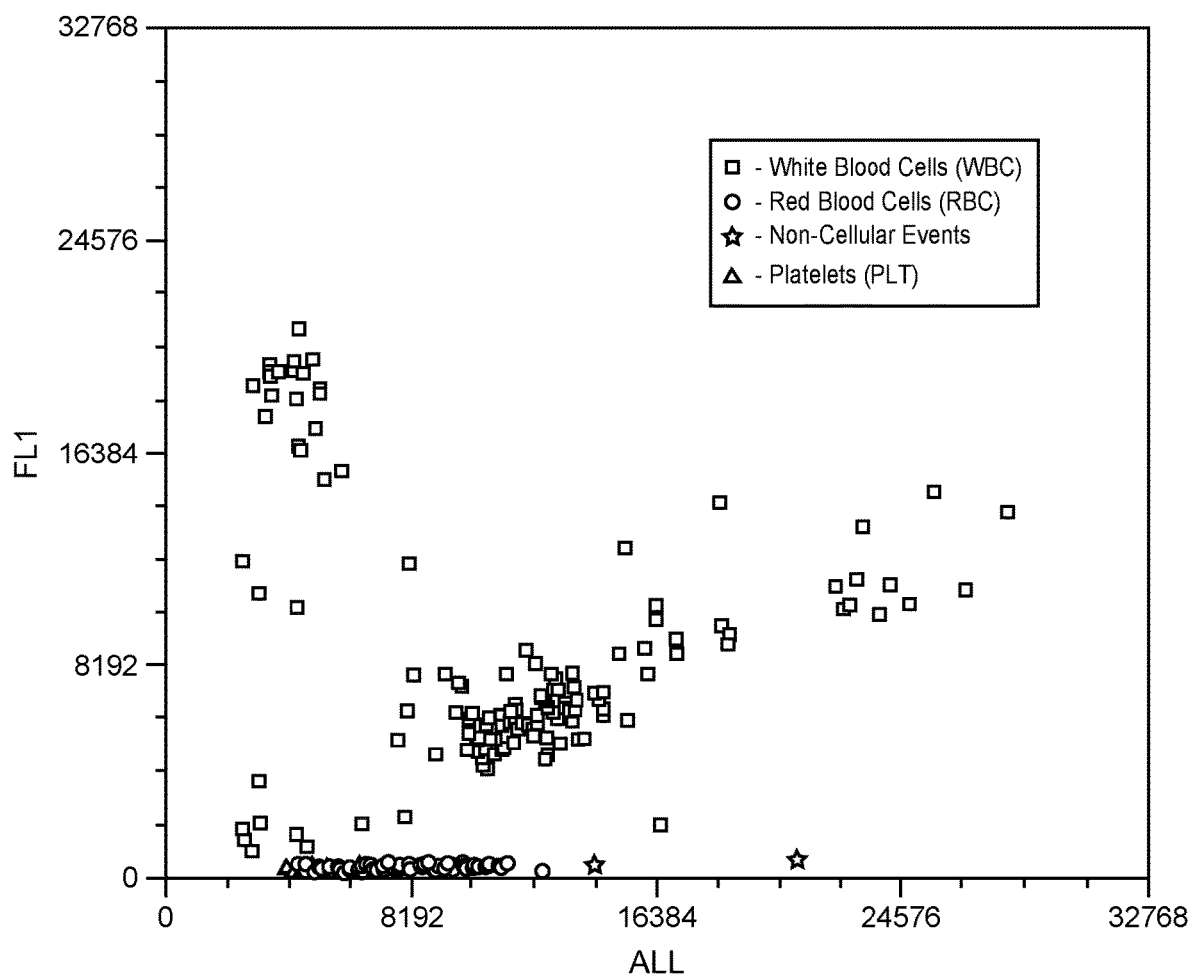
FIG. 2B is a scattergram (FL1 v. ALL) of cellular analysis for a body fluid sample. WBCs and RBCs are well separated in fluorescence (FL1). WBC=89/µL (reference=81/µL); RBC=2012/µL (reference=1733/µL).
Figure 3A:
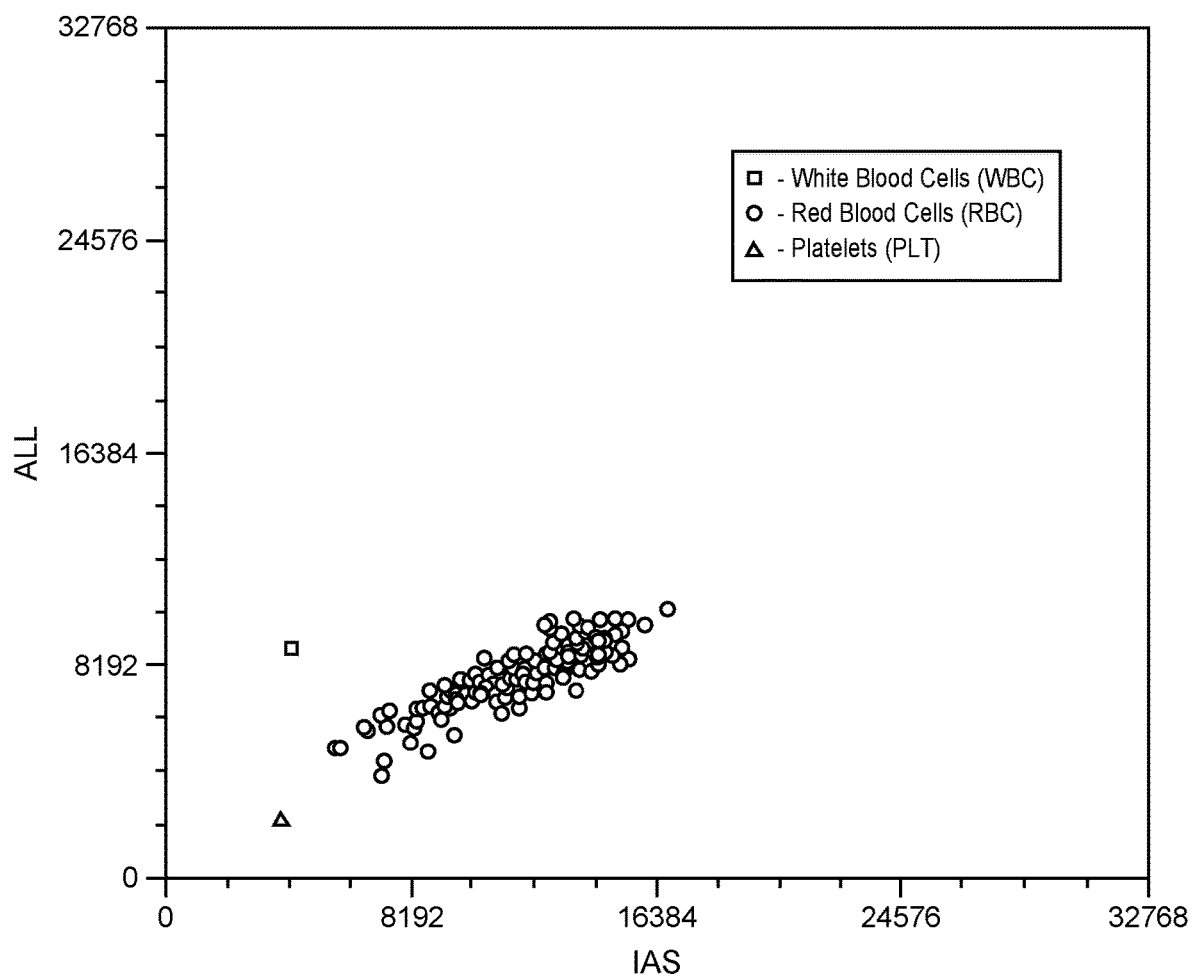
FIG. 3A is a scattergram (ALL v. IAS) of cellular analysis of another body fluid sample. WBC=0.95/µL (reference=0.33/µL); RBC=142/µL (reference=122/µL).
Figure 3B:
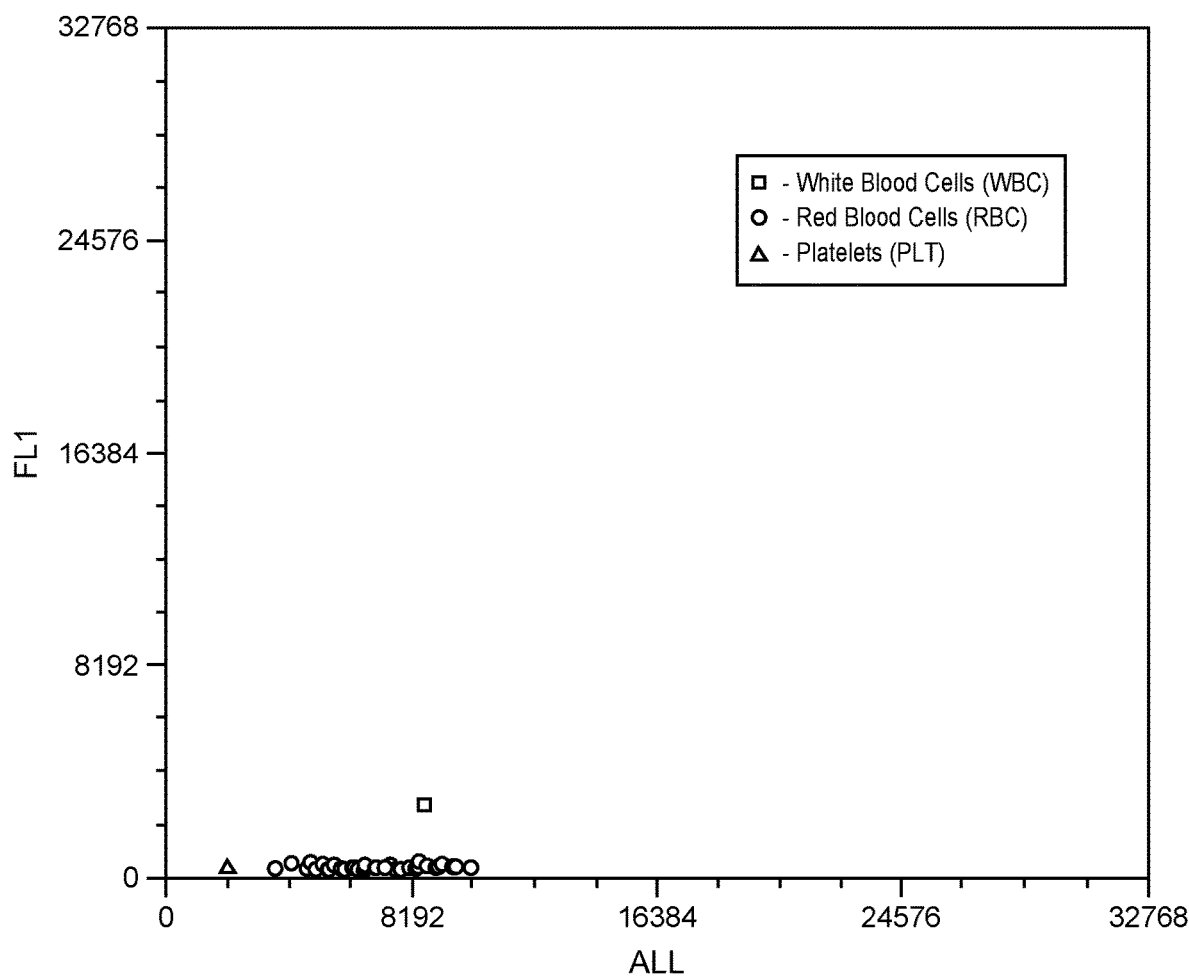
FIG. 3B is a scattergram (FL1 v. ALL) of cellular analysis of another body fluid sample. WBCs and RBCs are well separated in fluorescence (FL1). WBC=0.95/µL (reference=0.33/µL); RBC=142/µL (reference=122/µL).
Figure 4A:
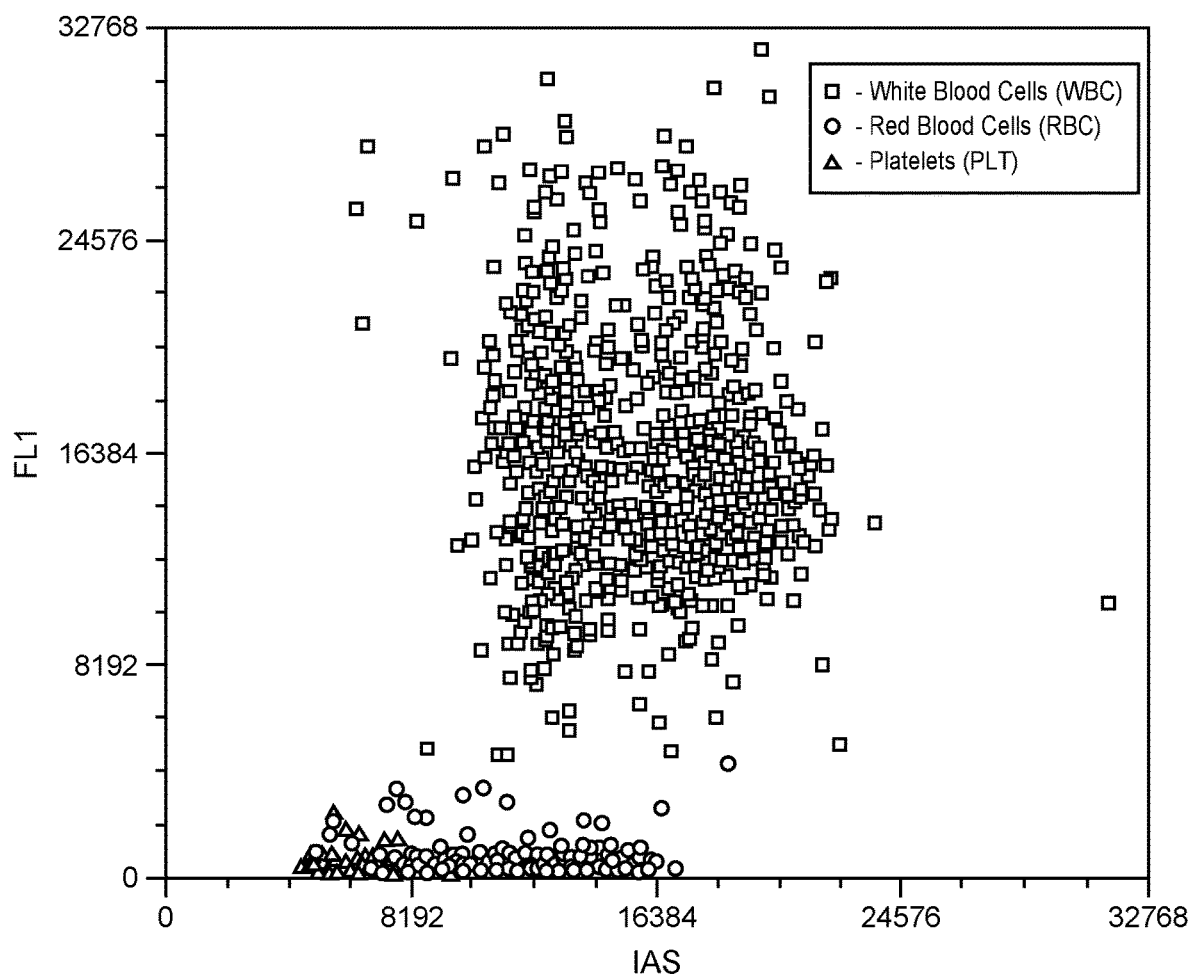
FIG. 4A is an FL1 v. IAS scattergram of the first dilution of a six level serial dilution of a buffy coat sample. The original buffy coat sample contains $6.1 \times 10^3$/µL WBC and $15 \times 10^3$/µL RBC. The six levels, (A), (B), (C), (D), (E) and (F), were prepared based upon 1:10, 1:30, 1:100, 1:300, 1:1000 and 1:3000, respectively, dilutions with PBS. All samples were measured using a dilution on a prototype analyzer.
Figure 4B:
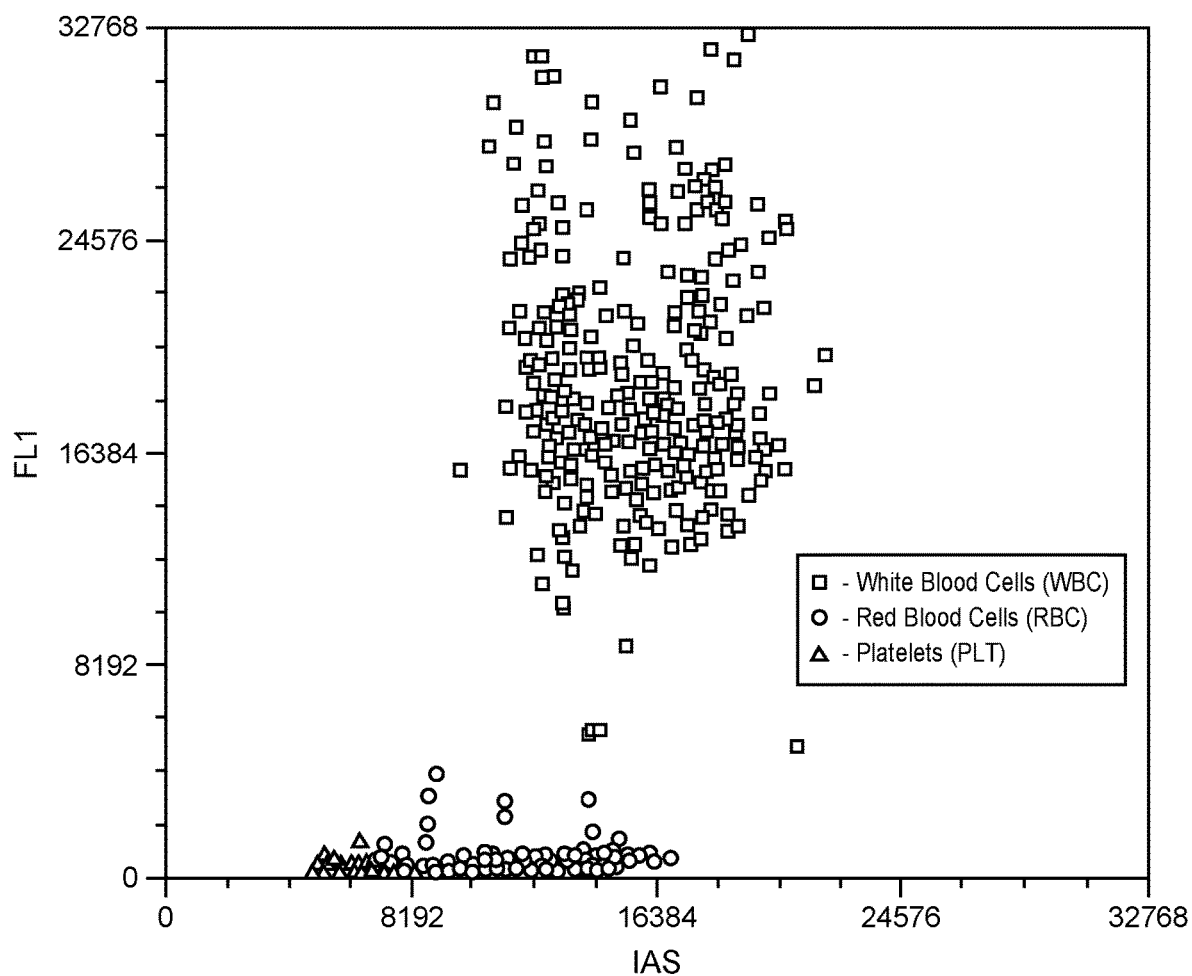
FIG. 4B is an FL1 v. IAS scattergram of the second dilution of a six level serial dilution of a buffy coat sample. The original buffy coat sample contains $6.1 \times 10^3$/µL WBC and $15 \times 10^3$/µL RBC. The six levels, (A), (B), (C), (D), (E) and (F), were prepared based upon 1:10, 1:30, 1:100, 1:300, 1:1000 and 1:3000, respectively, dilutions with PBS. All samples were measured using a dilution on a prototype analyzer.
Figure 4C:
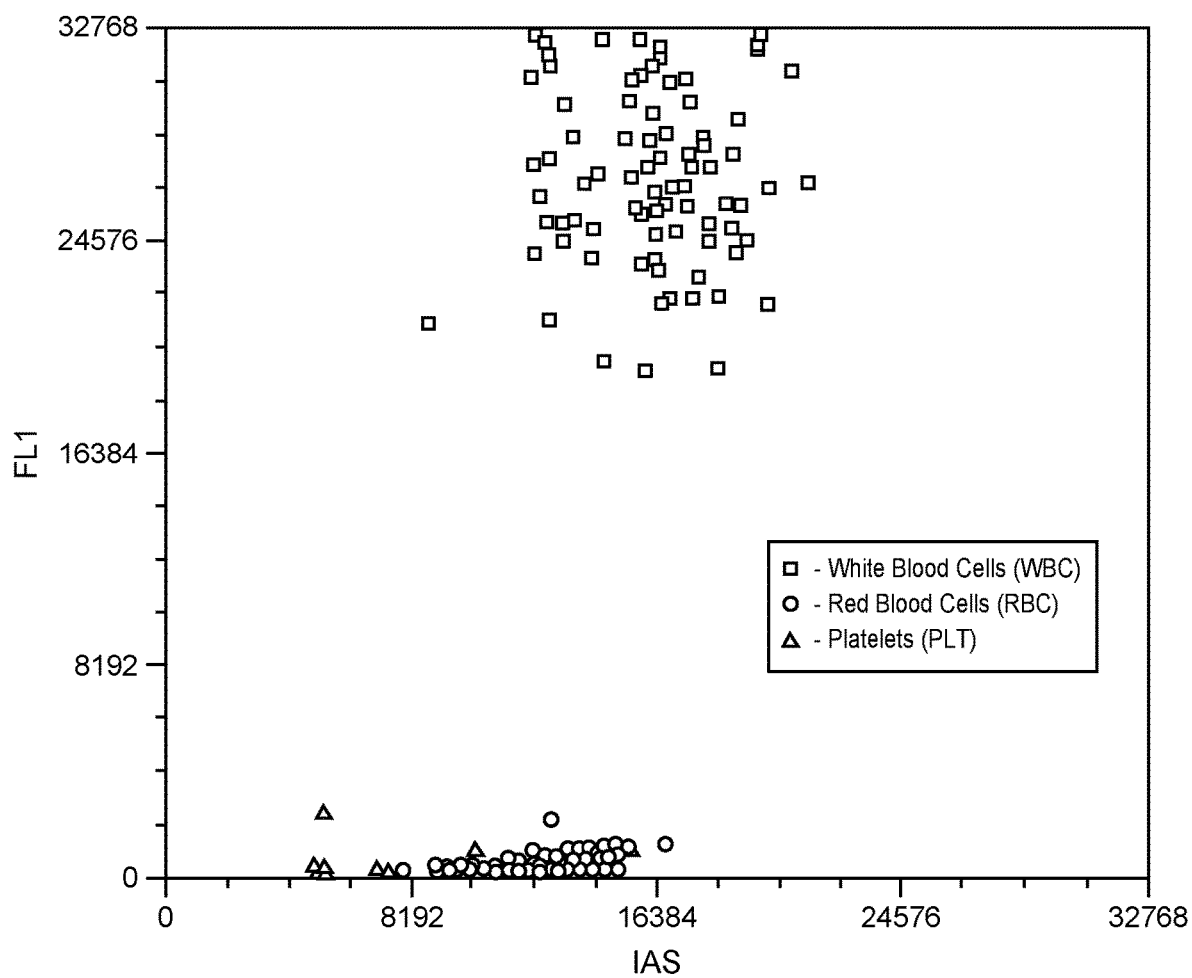
FIG. 4C is an FL1 v. IAS scattergram of the third dilution of a six level serial dilution of a buffy coat sample. The original buffy coat sample contains $6.1 \times 10^3$/µL WBC and $15 \times 10^3$/µL RBC. The six levels, (A), (B), (C), (D), (E) and (F), were prepared based upon 1:10, 1:30, 1:100, 1:300, 1:1000 and 1:3000, respectively, dilutions with PBS. All samples were measured using a dilution on a prototype analyzer.
Figure 4D:
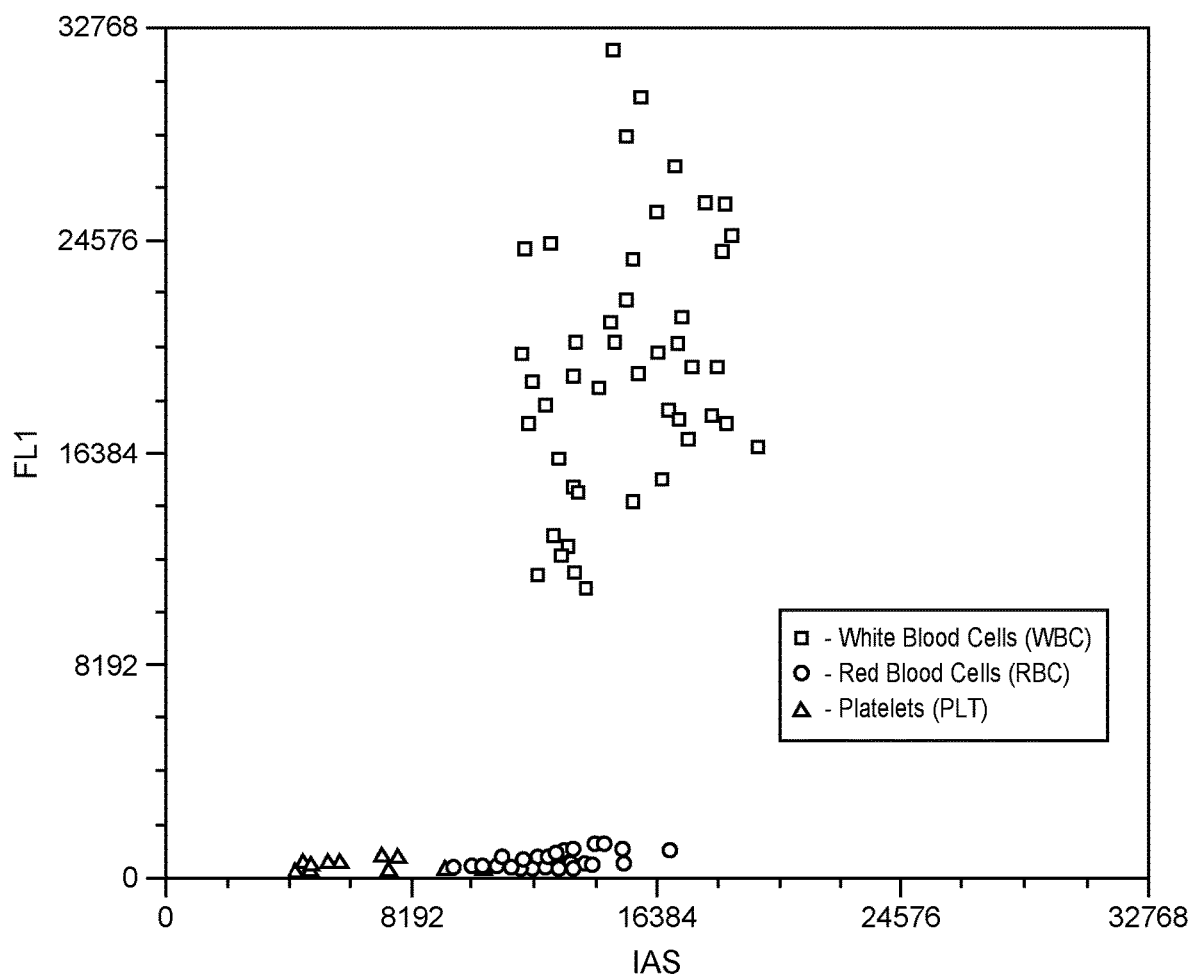
FIG. 4D is an FL1 v. IAS scattergram of the fourth dilution of a six level serial dilution of a buffy coat sample. The original buffy coat sample contains $6.1 \times 10^3$/µL WBC and $15 \times 10^3$/µL RBC. The six levels, (A), (B), (C), (D), (E) and (F), were prepared based upon 1:10, 1:30, 1:100, 1:300, 1:1000 and 1:3000, respectively, dilutions with PBS. All samples were measured using a dilution on a prototype analyzer.
Figure 4E:
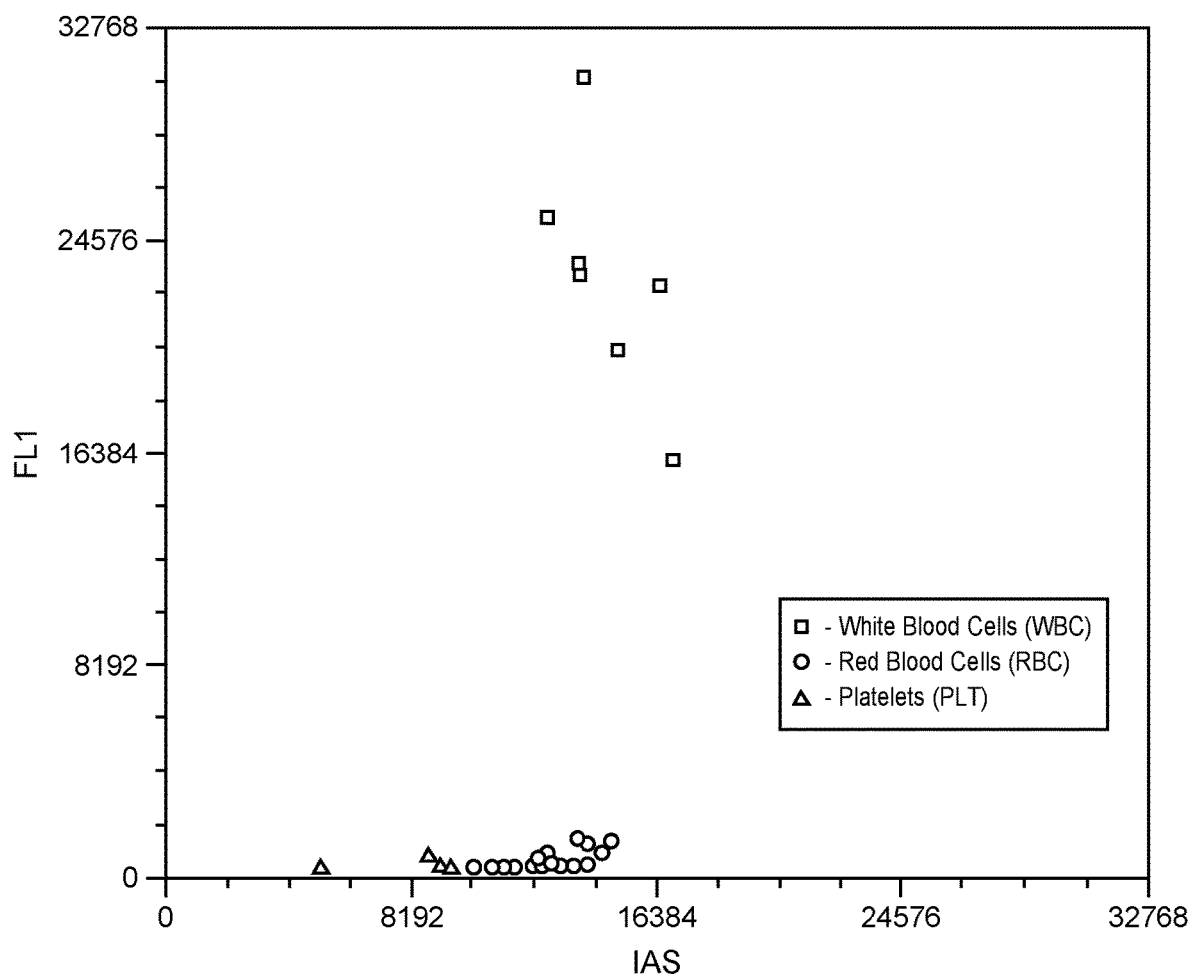
FIG. 4E is an FL1 v. IAS scattergram of the fifth dilution of a six level serial dilution of a buffy coat sample. The original buffy coat sample contains $6.1 \times 10^3$/µL WBC and $15 \times 10^3$/µL RBC. The six levels, (A), (B), (C), (D), (E) and (F), were prepared based upon 1:10, 1:30, 1:100, 1:300, 1:1000 and 1:3000, respectively, dilutions with PBS. All samples were measured using a dilution on a prototype analyzer.
Figure 4F:
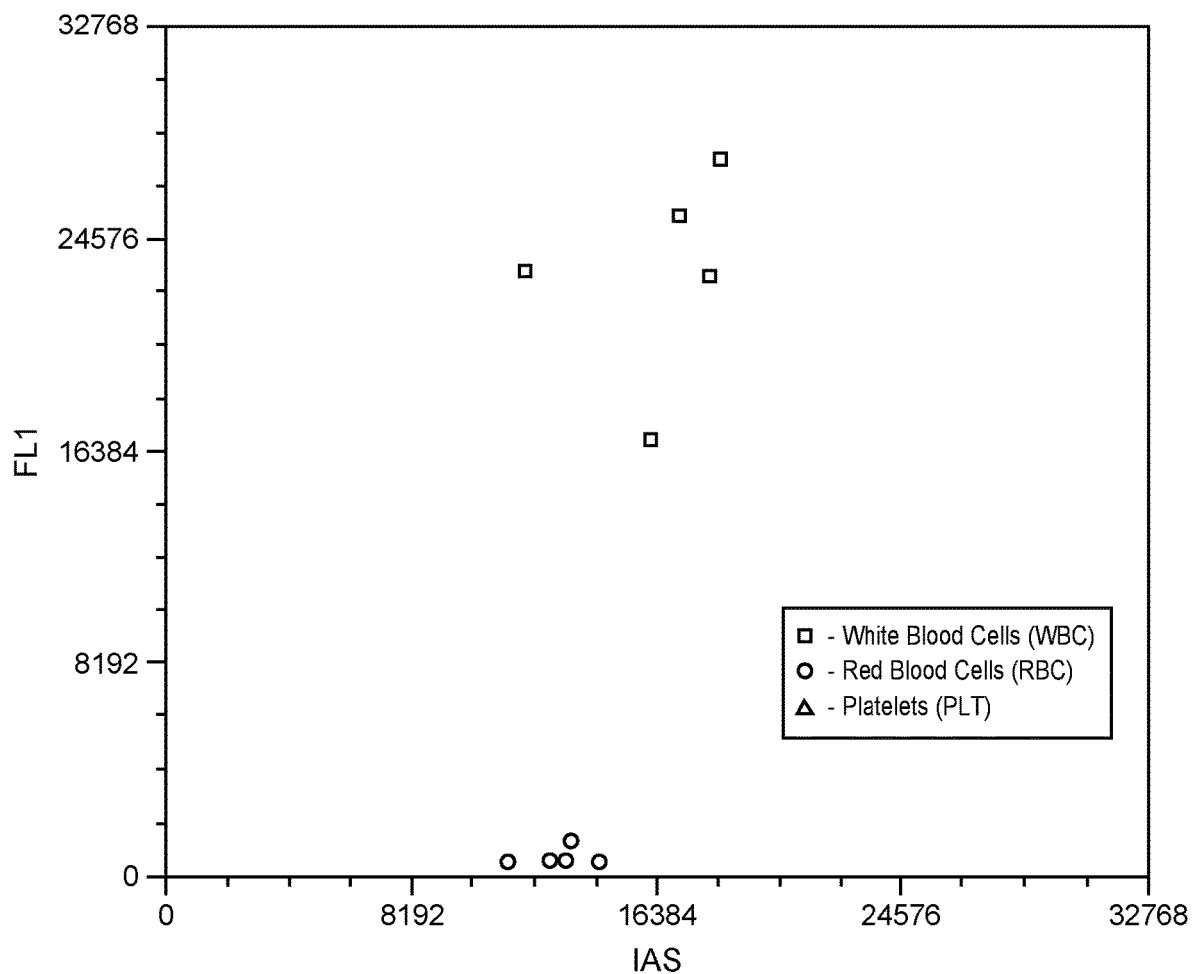
FIG. 4F is an FL1 v. IAS scattergram of the sixth dilution of a six level serial dilution of a buffy coat sample. The original buffy coat sample contains $6.1 \times 10^3$/µL WBC and $15 \times 10^3$/µL RBC. The six levels, (A), (B), (C), (D), (E) and (F), were prepared based upon 1:10, 1:30, 1:100, 1:300, 1:1000 and 1:3000, respectively, dilutions with PBS. All samples were measured using a dilution on a prototype analyzer.

FIGS. 2A and 2B show scattergrams of cellular analysis of a body fluid sample. The cells were enumerated after analysis: WBC=89/µL (reference=81/µL); RBC=2012/µL (reference=1733/µL). FIGS. 3A and 3B show scattergrams of cellular analysis of another body fluid sample. The cells were enumerated after analysis: WBC=0.95/μL (reference=0.33/μL); RBC=142/μL (reference=122/μL).

Example 2

Analysis of Very Low Cell Count Samples

Figure 5:
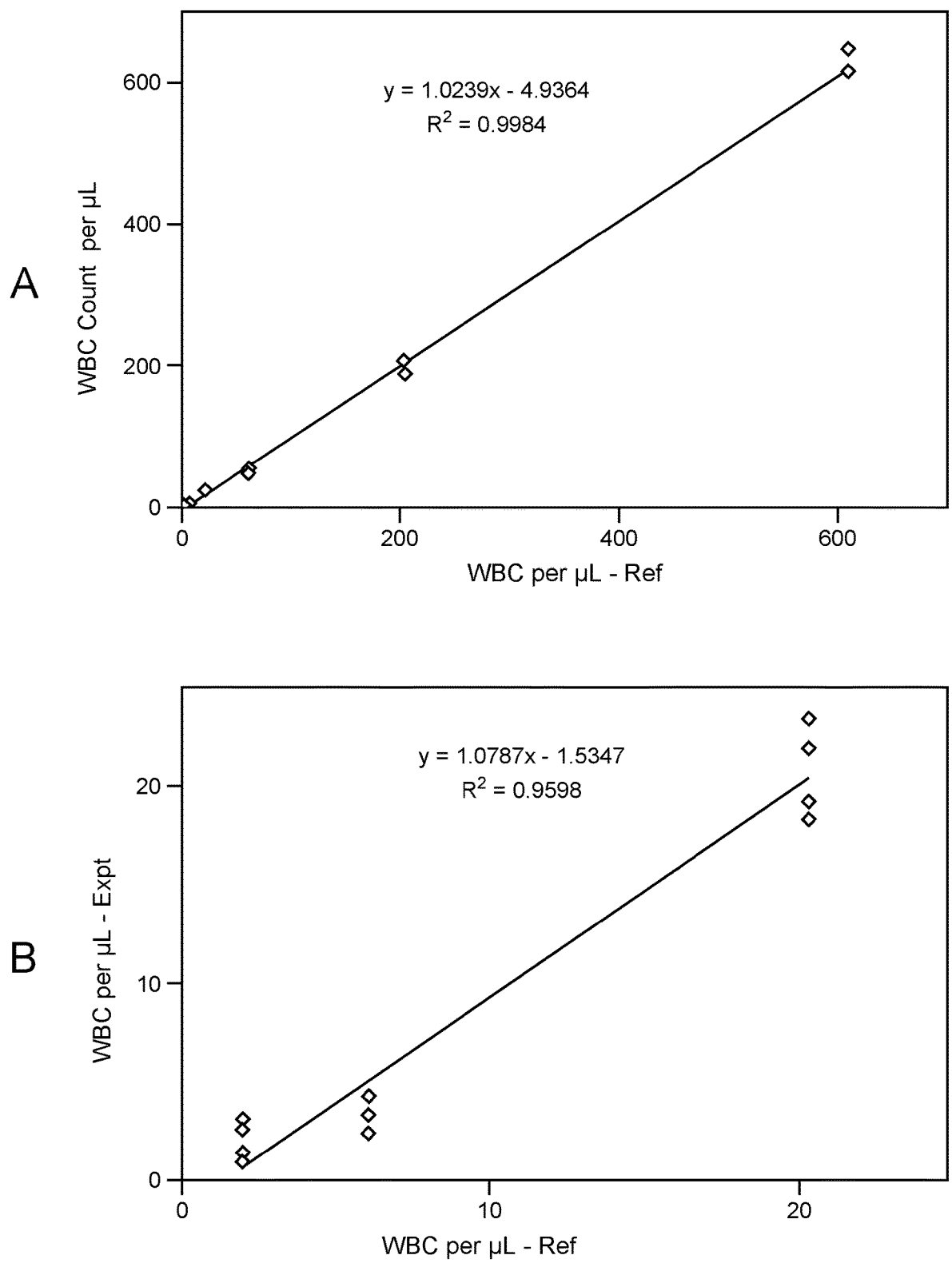
FIG. 5 provides correlation graphs of WBC (measured vs. calculated) among all six levels of diluted buffy coat samples (A) and three low-end samples only (B). Multiple dots at each level indicate that multiple runs were performed. The overall correlations were: Y=1.0239 X−4.9 ($R^2$=0.9984) for all six levels and Y=1.0787 X−1.5 ($R^2$=0.9598) for the three levels with the lowest cell concentrations.

The detection limit was further validated in a study using diluted buffy coat samples. Six levels of diluted buffy coat samples were prepared using serial dilutions. FL1 vs. IAS scattergrams for the six levels of diluted buffy coat samples are shown in FIGS. 4A-4F. FIG. 5 shows the correlation of WBC (measured vs. calculated). Very good correlations were achieved: (A) Y=1.0239 X−4.9 ($R^2$=0.9984) for all six levels and (B) Y=1.0787 X−1.5 ($R^2$=0.9598) for the three levels with lowest cell concentrations.

Example 3

Cellular Analysis of Body Fluid Samples at Dilution Ratio of 1:35

A comprehensive body fluid study was conducted to evaluate the methods provided herein. A total of 91 body fluid specimens, including CSF, plural, peritoneal, and ascites fluids, were measured and analyzed on a prototype analyzer with 1:35 (blood:reagent) dilution ratio, 2.3 μL per second injection rate, and 32 seconds sample measurement (data collection). Reference values of WBC and RBC were achieved by manual chamber counting.

Figure 6:
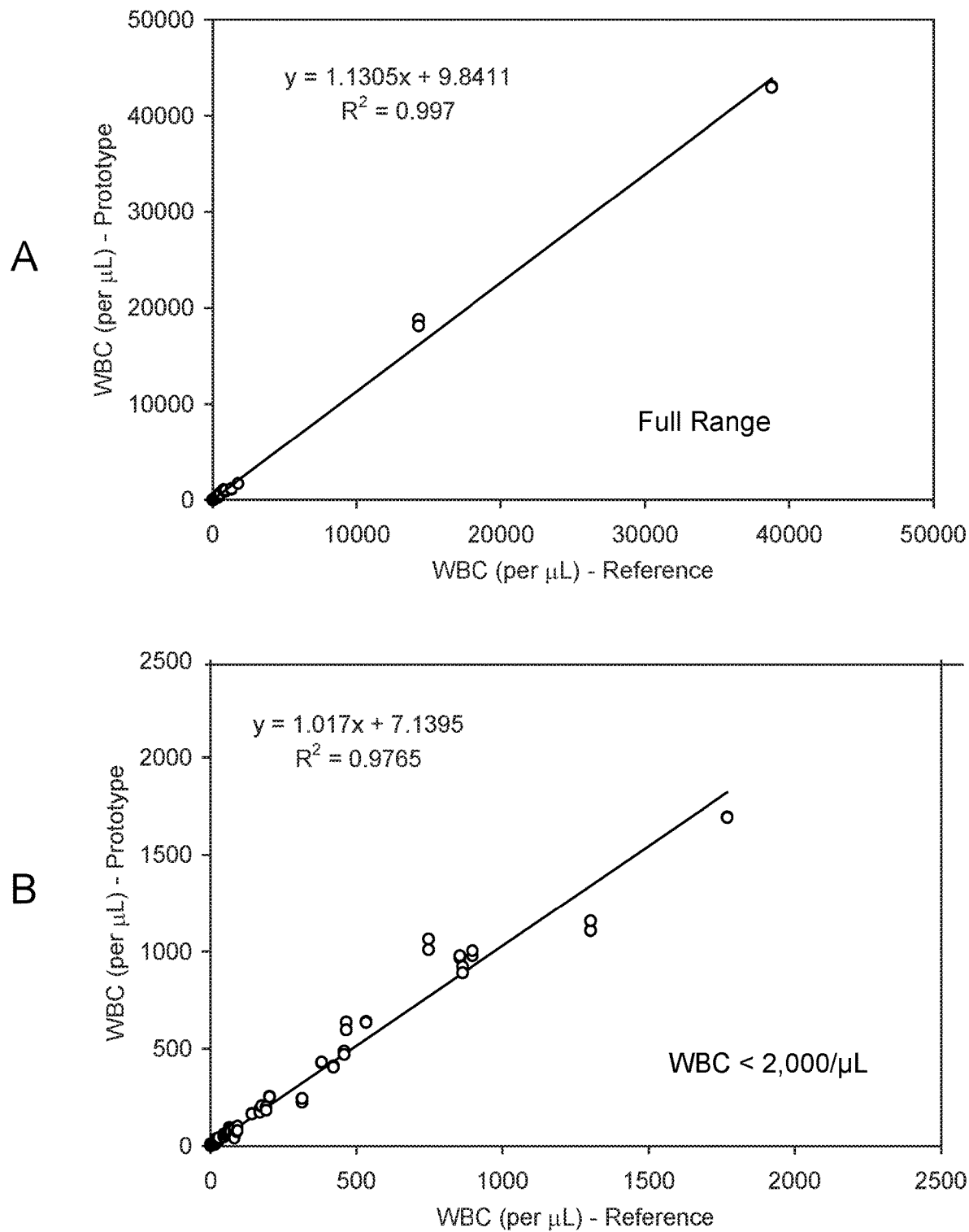
FIG. 6 provides correlation graphs of WBC (current method vs. reference) for 91 body fluid samples. The correlations were plotted in different ranges: (A) full range (~40,000/µL), (B) <2,000/µL, (C)<200/µL and (D)<50/µL. The dilution ratio was 1:35 (specimen to labeling reagent).
Figure 6:
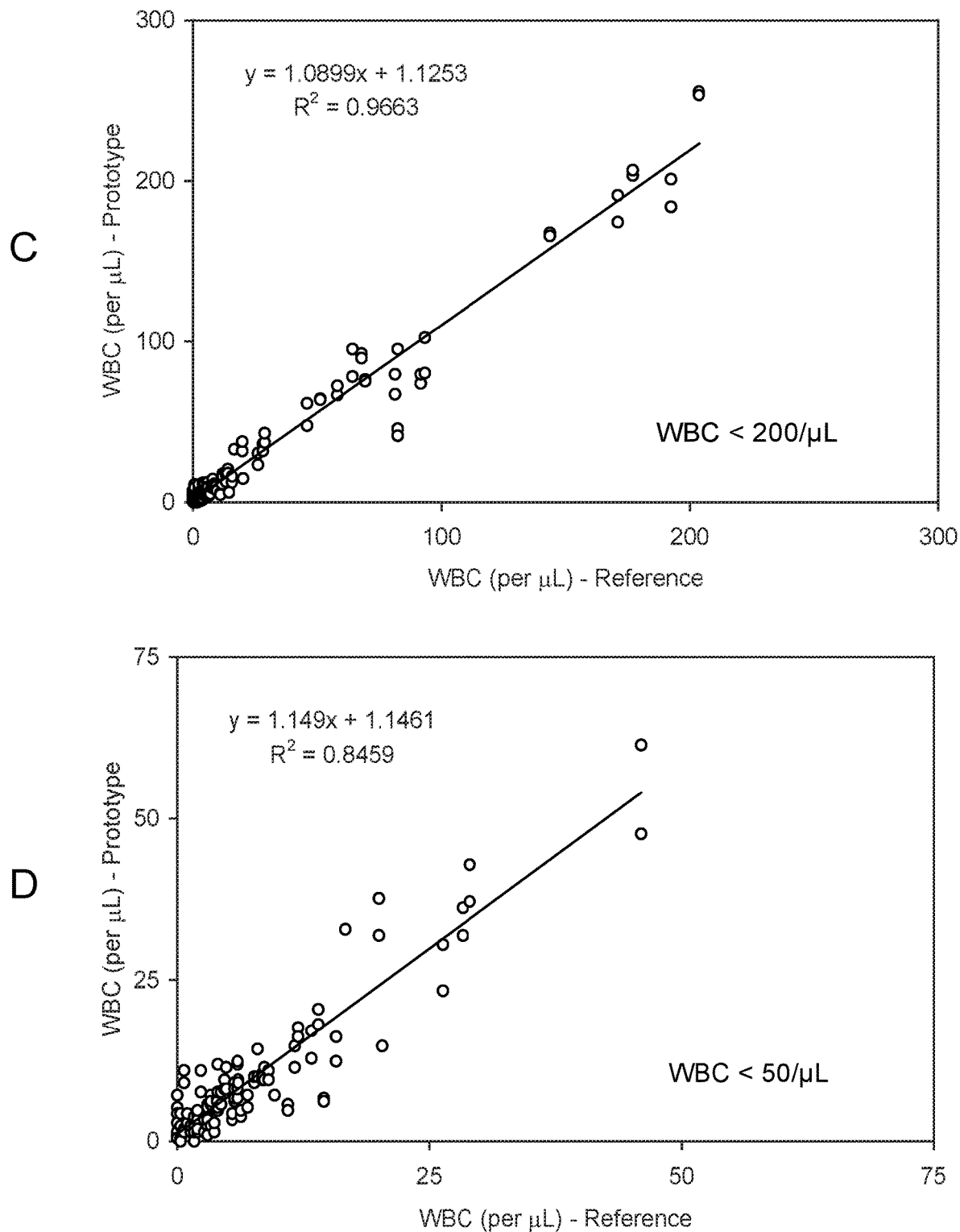
Figure 7:
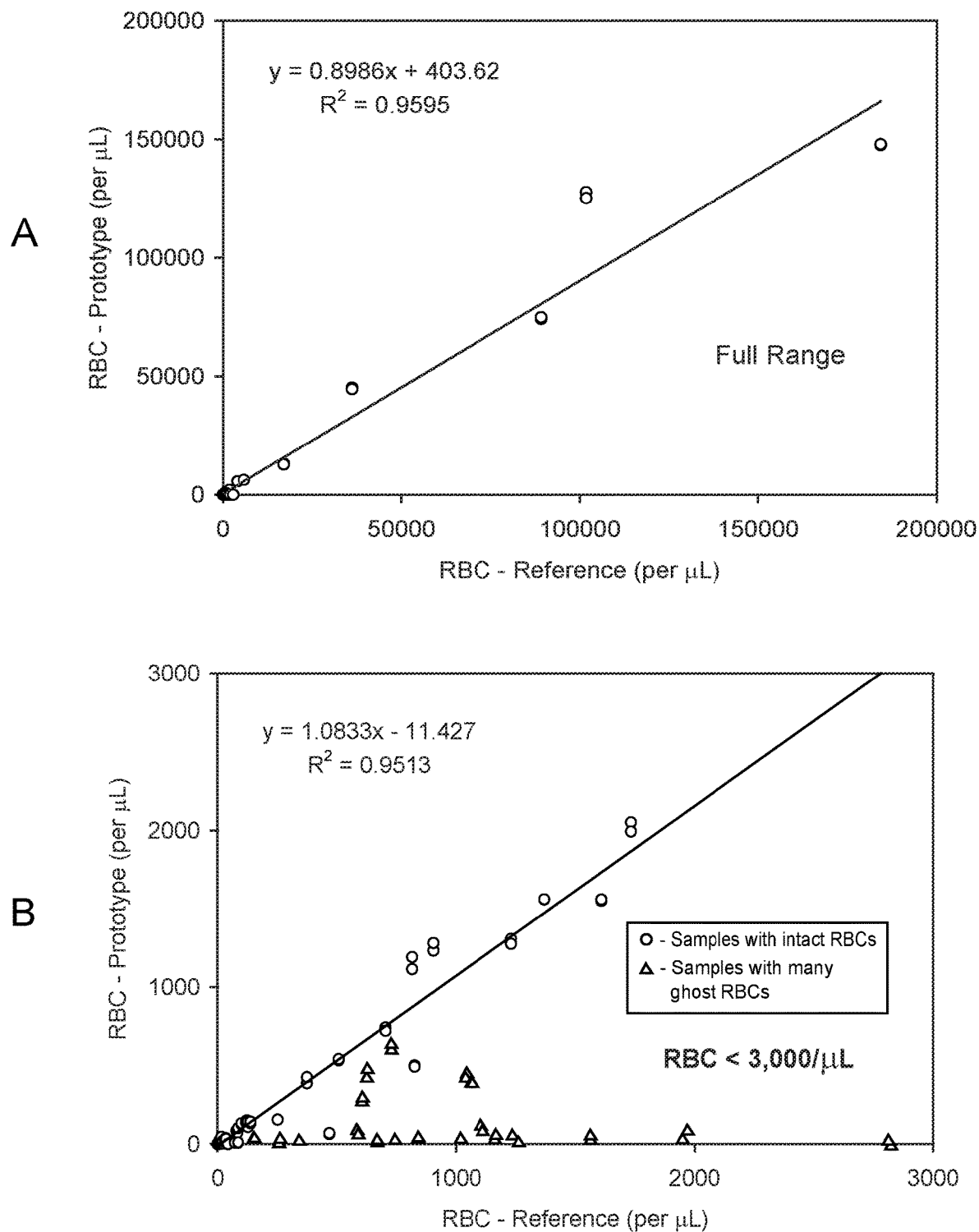
FIG. 7 provides correlation graphs of RBC (current method vs. reference) for 91 body fluid samples. The correlations were plotted in different ranges: (A) full range (~200,000/µL), (B) <3,000/µL, (C) <200/µL and (D) <50/µL. Samples with many RBC ghosts were not included in the correlation analysis. The dilution ratio was 1:35 (specimen to labeling reagent).
Figure 7:
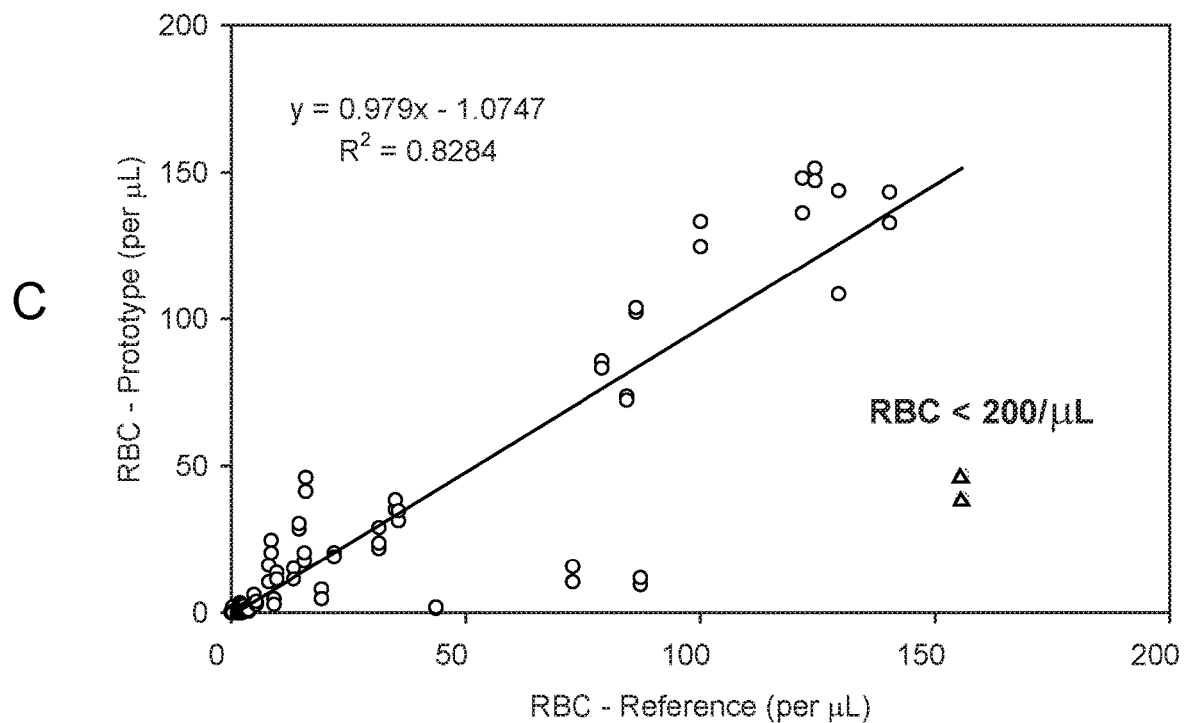
Figure 7:
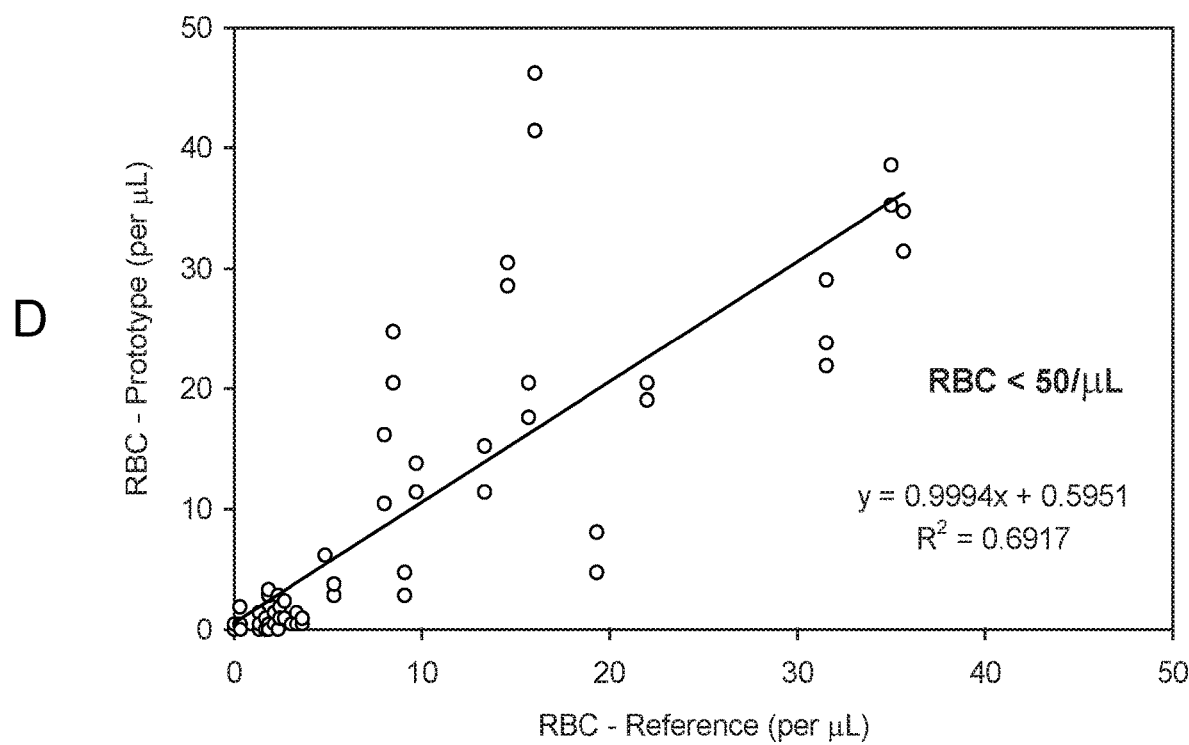

Excellent correlations in WBC were achieved between the methods described above and the reference method (FIG. 6): (A) Y=1.1305 X−9.8411, $R^2$=0.997 (Full range, up to approximately 40,000/μL); (B) Y=1.017 X+7.1395, $R^2$=0.9765 (<2,000/μL); (C) Y=1.0899 X+1.1253, $R^2$=0.9663 (<200/μL); and (D) Y=1.149 X+1.1461, $R^2$=0.8459 (<50/μL). Very good correlations in RBC were achieved between the methods described above and the reference method (FIG. 7): (A) Y=0.8996 X+403.62, $R^2$=0.9595 (Full range, up to approximately 200,000/μL); (B) Y=1.0833 X−11.427, $R^2$=0.9513 (<3,000/μL); (C) Y=0.979 X−1.0747, $R^2$=0.8284 (<200/μL); and (D) Y=0.9994 X+0.5951, $R^2$=0.6917 (<50/μL). For RBC analysis, the samples with many RBC ghosts were not included in the correlation analysis.

Example 4

Cellular Analysis of Body Fluid Samples at Dilution Ratio of 1:10

Another comprehensive body fluid study was conducted to evaluate the methods provided herein. A total of 155 body fluid specimens, including CSF, plural, peritoneal, and ascites fluids, were measured and analyzed on a prototype analyzer with 1:10 (blood:reagent) dilution ratio, 2.3 μL per second injection rate, and 32 seconds sample measurement (data collection). Reference values of WBC and RBC were achieved by manual chamber counting.

Figure 8:
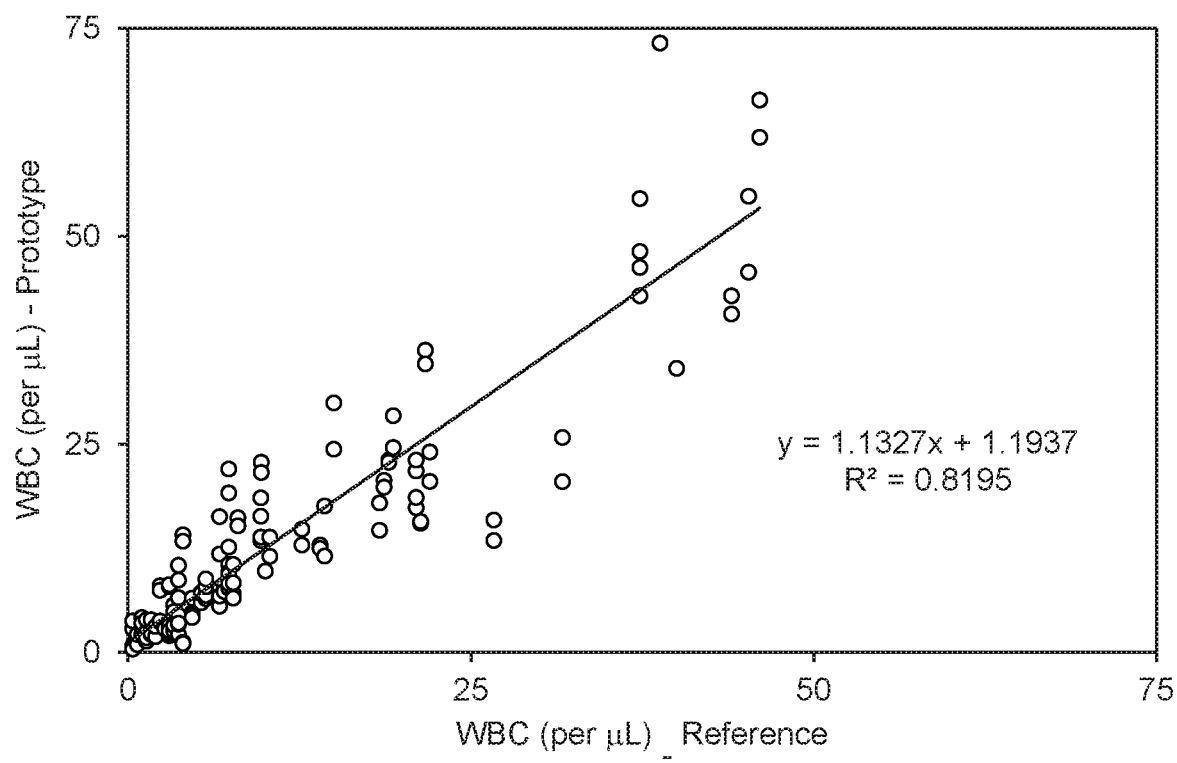
FIG. 8 is a correlation graph of WBC (invented method vs. reference) for 72 body fluid samples with very low cell concentrations (WBC<50/µL). The dilution ratio was 1:10 (specimen to labeling reagent).
Figure 9:
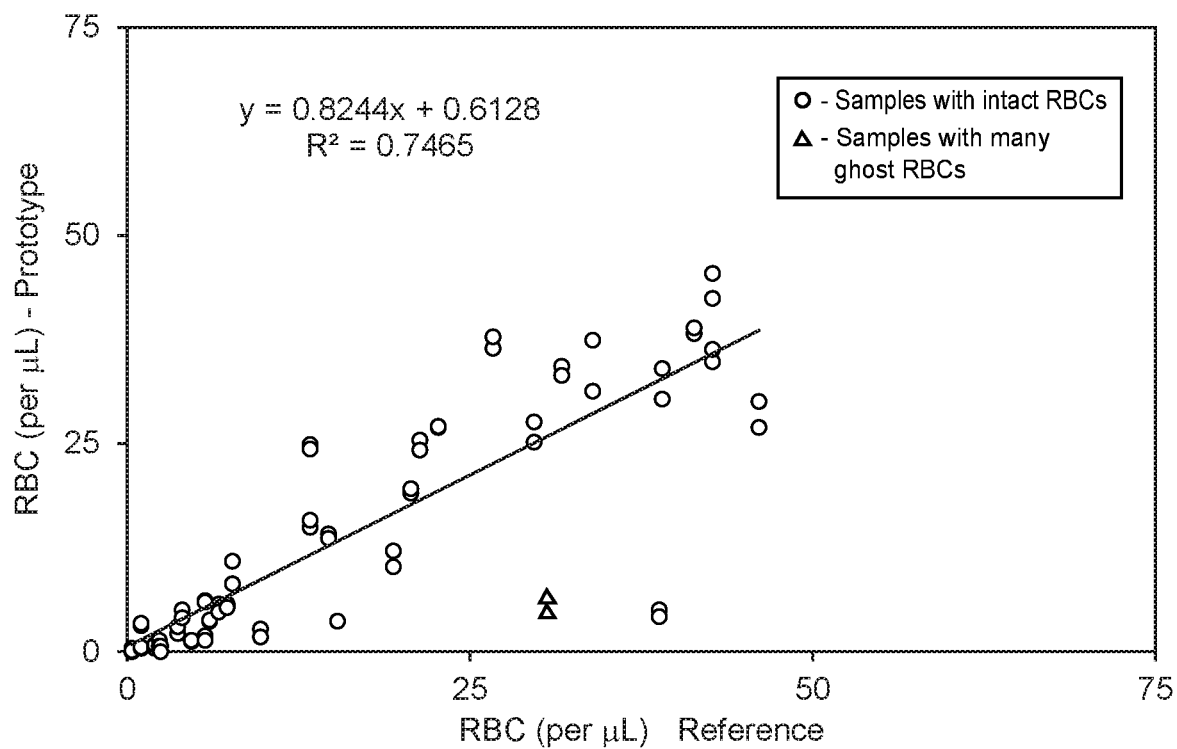
FIG. 9 is a correlation graph of RBC (current method vs. reference) for 38 body fluid samples with very low cell concentrations (RBC<50/µL). Samples with many RBC ghosts were not included in correlation analysis. The dilution ratio was 1:10 (specimen to labeling reagent).

Excellent correlations in WBC were achieved, even for the samples with low-end WBC concentrations, between the methods described above and the reference method (FIG. 8): Y=1.1327 X+1.1937, $R^2$=0.8195 (WBC<50/μL, 72 samples). Very good correlations in WBC were achieved, even for the samples with low-end RBC concentrations, between the methods described above and the reference method (FIG. 9): Y=0.8244 X+0.6128, $R^2$=0.7465 (RBC<50/μL, 38 samples). For RBC analysis, the body samples with many RBC ghosts were not included in the correlation analysis.

That which is claimed is:

1. A method for analyzing in a flow cytometer a body fluid containing cells, the method comprising:
   staining the body fluid with a fluorescent dye, wherein the fluorescent dye permeates a cell membrane and binds to a nucleic acid to form a dye complex within the cell;
   irradiating the stained body fluid with energy from an energy source;
   measuring a fluorescence signal emitted by the dye complex in the stained body fluid; and
   differentiating cells with nuclei from cells without nuclei based only on the presence or absence of the fluorescent dye.

2. The method of claim 1, wherein the body fluid comprises fewer than about 20 cells/μL.

3. The method of claim 1, wherein the body fluid comprises greater than about 20 cells/μL.

4. The method of claim 1, wherein the nucleic acid is a DNA or an RNA.

5. The method of claim 1, wherein the energy source produces monochromatic light having a wavelength in the visible spectrum, and wherein the wavelength of the monochromatic light and the wavelength of the fluorescence signal are different.

6. The method of claim 1, wherein unbound fluorescent dye emits less fluorescent light when irradiated with energy from the energy source compared with the dye complex.

7. The method of claim 1, wherein unbound fluorescent dye does not fluoresce when irradiated with energy from the energy source while unbound to the nucleic acid, such that cells lacking the dye complex do not emit a fluorescent signal.

8. The method of claim 1, wherein the differentiating involves enumerating and differentiating red blood cells (RBCs) and white blood cells (WBCs).

9. The method of claim 1, wherein the method does not involve lysing RBCs prior to the measuring.

10. The method of claim 1, wherein the body fluid comprises intact WBCs and RBCs.

11. The method of claim 1, wherein the flow cytometer is an automated hematology analyzer.

12. The method of claim 1, wherein the measuring comprises flowing the body fluid through a flow cell in the flow cytometer.

13. The method of claim 1, wherein the fluorescent dye is provided in a composition that further comprises water.

14. The method of claim 1, further comprising separating, in the flow cytometer, cells with nuclei from cells without nuclei based only on the presence or absence of the fluorescent dye.

15. A method for differentiating white blood cells (WBCs) from the red blood cells (RBCs) in a flow cytometer, the cells suspected to be in a sample of a body fluid, the method comprising:
   contacting the sample of body fluid suspected of containing the cells with a solution comprising a fluorescent dye, wherein the fluorescent dye is water soluble, permeates a cell membrane, and binds to a nucleic acid;
   irradiating the cells with an excitation light from an excitation light source;
   measuring light emissions from the cells; and
   differentiating the WBCs from the RBCs based only on the presence or absence of the fluorescent dye.

16. The method of claim 15, further comprising separating, in the flow cytometer, the WBCs from the RBCs.

\* \* \* \* \*

UNITED STATES PATENT AND TRADEMARK OFFICE
CERTIFICATE OF CORRECTION

PATENT NO. : 10,774,359 B2
APPLICATION NO. : 15/979230
DATED : September 15, 2020
INVENTOR(S) : Jiong Wu et al.

Page 1 of 1

It is certified that error appears in the above-identified patent and that said Letters Patent is hereby corrected as shown below:

In the Claims

In Column 14, Line 56, Claim 15 please delete "the" (first occurrence).

Signed and Sealed this
Twentieth Day of October, 2020

Andrei Iancu
*Director of the United States Patent and Trademark Office*